(12) United States Patent
Wang et al.

(10) Patent No.: US 10,017,475 B2
(45) Date of Patent: Jul. 10, 2018

(54) ANTI-VASCULATURE AND ANTI-TUBULIN COMBRETASTATIN ANALOGS FOR TREATMENT OF CANCER

(71) Applicant: XAVIER UNIVERSITY OF LOUISIANA, New Orleans, LA (US)

(72) Inventors: Guangdi Wang, New Orleans, LA (US); Shilong Zheng, New Orleans, LA (US); Qiu Zhong, New Orleans, LA (US); Qiang Zhang, Metairie, LA (US)

(73) Assignee: XAVIER UNIVERSITY OF LOUSIANA, New Orleans, LA (US)

( * ) Notice: Subject to any disclaimer, the term of this patent is extended or adjusted under 35 U.S.C. 154(b) by 0 days.

(21) Appl. No.: 15/129,785

(22) PCT Filed: Mar. 26, 2015

(86) PCT No.: PCT/US2015/022624
§ 371 (c)(1),
(2) Date: Sep. 27, 2016

(87) PCT Pub. No.: WO2015/153252
PCT Pub. Date: Oct. 8, 2015

(65) Prior Publication Data
US 2017/0044103 A1    Feb. 16, 2017

Related U.S. Application Data

(60) Provisional application No. 61/972,749, filed on Mar. 31, 2014.

(51) Int. Cl.
*A61K 31/4418* (2006.01)
*C07D 213/61* (2006.01)
*A61K 45/06* (2006.01)
*C07D 213/30* (2006.01)
*A61K 31/4425* (2006.01)

(52) U.S. Cl.
CPC ........ *C07D 213/61* (2013.01); *A61K 31/4418* (2013.01); *A61K 31/4425* (2013.01); *A61K 45/06* (2013.01); *C07D 213/30* (2013.01)

(58) Field of Classification Search
CPC ................ C07D 213/61; C07D 213/30; A61K 31/4425; A61K 45/06; A61K 31/4418
See application file for complete search history.

(56) References Cited

U.S. PATENT DOCUMENTS

2012/0128693 A1* 5/2012 Byers ................... C07D 213/30
424/172.1

OTHER PUBLICATIONS

Xu; Chem. Eur. J. 2009, 15, 13105-13110.*
Tagat; Bioorganic & Medicinal Chemistry Letters 1995, 5, 2143-2146.*

(Continued)

*Primary Examiner* — Daniel R Carcanague
(74) *Attorney, Agent, or Firm* — McBee Moore Woodward & Vanik IP, LLC; Susan McBee; Chester Moore

(57) ABSTRACT

Combretastatins analog compounds and their pharmaceutically acceptable salts are presented, as well as pharmaceutical compositions comprising the combretastatin analog compounds and uses of the combretastatin analog compounds, either alone or in combination with at least one additional therapeutic agent, in the treatment of cancer, and in particular cancer presenting as metastatic tumors.

11 Claims, 10 Drawing Sheets

2-(2,4-Dimethoxyphenyl)-6-(3-hydroxy-4-methoxyphenyl) pyridin-1-ium chloride (Cmpd 5)

(56) References Cited

OTHER PUBLICATIONS

Jacquemard; European Journal of Medicinal Chemistry 40, 2005, 1087-1095.*
Tron; J. Med. Chem. 2006, 49, 3033-3044.*
Shan; Current Medicinal Chemistry, 2011, 18, 523-538.*
Semenov; J. Nat. Prod., 2010, 73 1796-1802.*
Brown; Top Heterocycl Chem 2006, 2, 1-51.*
Simoni; J. Med. Chem. 2005, 48, 723-736.*
Zheng, Shilong et. al., "Design, Synthesis, and Biological Evaluation of Novel Pyridine-Bridged Analogues of Combretastatin-A4 as Anticancer Agents", Journal of Medicinal Chemistry, Mar. 26, 2014, pp. 3369-3381, vol. 57, No. 8.
International Search Report of International Patent Application No. PCT/US2015/022624 dated May 26, 2015.

* cited by examiner 2-bromo-6-(3,4,5-trimethoxyphenyl)pyridine
(Cmpd 2a)

2-bromo-6-(3,4-dimethoxyphenyl)pyridine
(Cmpd 2b)

2-bromo-6-(2,4-dimethoxyphenyl)pyridine
(Cmpd 2c)

2-bromo-6-(4-methoxyphenyl)pyridine
(Cmpd 2d)

5-bromo-2-(3,4,5-trimethoxyphenyl)pyridine
(Cmpd 2e)

5-Bromo-2-(2,4-dimethoxyphenyl)pyridine
(Cmpd 2f)

2,6-bis(3,4,5-trimethoxyphenyl)pyridine
(Cmpd 3a)

2,6-bis(3,4-dimethoxyphenyl)pyridine
(Cmpd 3b)

2,6-bis(2,4-dimethoxyphenyl)pyridine
(Cmpd 3c)

2,6-bis(4-methoxyphenyl)pyridine
(Cmpd 3d)

2,5-bis(3,4,5-trimethoxyphenyl)pyridine
(Cmpd 3e)

2,4-bis(3,4,5-trimethoxyphenyl)pyridine
(Cmpd 3f)

2,5-bis(2,4-dimethoxyphenyl)pyridine
(Cmpd 3g)

2,4-bis(2,4-dimethoxyphenyl)pyridine
(Cmpd 3h)

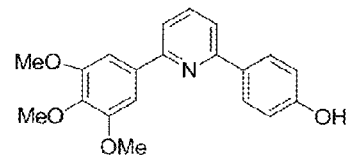

4-(6-(3,4,5-trimethoxyphenyl)pyridin-2-yl)phenol
(Cmpd 4a)

FIG. 15

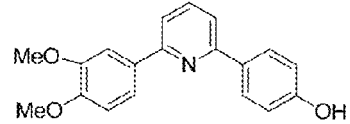

4-(6-(3,4-dimethoxyphenyl)pyridin-2-yl)phenol
(Cmpd 4b)

FIG. 16

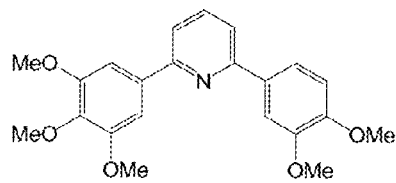

2-(3,4-Dimethoxyphenyl)-6-(3,4,5-trimethoxyphenyl)pyridine
(Cmpd 4c)

FIG. 17

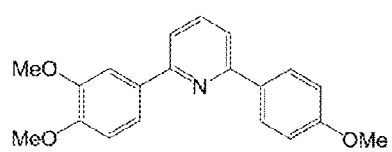

2-(3,4-Dimethoxyphenyl)-6-(4-methoxyphenyl)pyridine
(Cmpd 4d)

FIG. 18

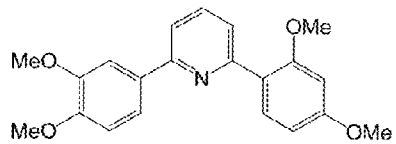

2-(2,4-Dimethoxyphenyl)-6-(3,4-dimethoxyphenyl)pyridine
(Cmpd 4e)

FIG. 19

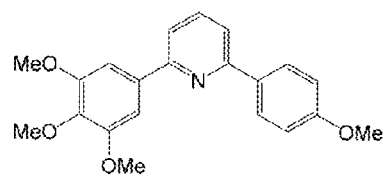

2-(4-Methoxyphenyl)-6-(3,4,5-trimethoxyphenyl)pyridine
(Cmpd 4f)

FIG. 20

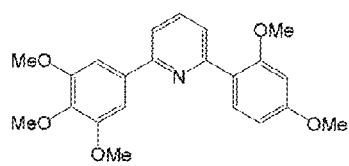

2-(2,4-Dimethoxyphenyl)-6-(3,4,5-trimethoxyphenyl)pyridine
(Cmpd 4g)

FIG. 21

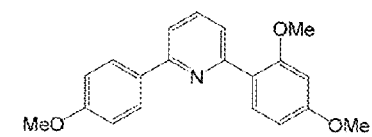

2-(2,4-Dimethoxyphenyl)-6-(4-methoxyphenyl)pyridine
(Cmpd 4h)

FIG. 22

5-(3,4-Dimethoxyphenyl)-2-(3,4,5-trimethoxyphenyl)pyridine
(Cmpd 4i)

4-(6-(4-methoxyphenyl)pyridin-2-yl)phenol
(Cmpd 4j)

4-(6-(2,4-dimethoxyphenyl)pyridin-2-yl)phenol
(Cmpd 4k)

2-(2,4-Dimethoxyphenyl)-6-(3,5-dimethoxyphenyl)pyridine
(Cmpd 4l)

2-(2,4-Dimethoxyphenyl)-6-(2,5-dimethoxyphenyl)pyridine
(Cmpd 4m)

2-(2,3-Dimethoxyphenyl)-6-(2,4-dimethoxyphenyl)pyridine
(Cmpd 4n)

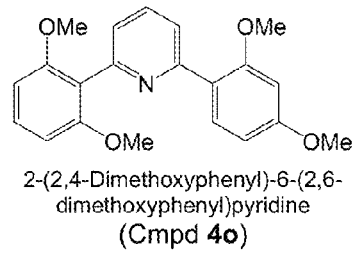

2-(2,4-Dimethoxyphenyl)-6-(2,6-dimethoxyphenyl)pyridine
(Cmpd 4o)

FIG. 29

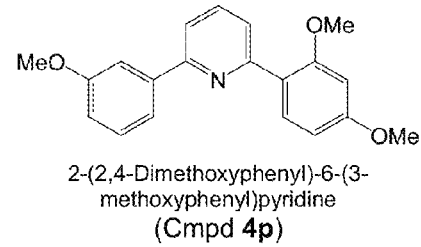

2-(2,4-Dimethoxyphenyl)-6-(3-methoxyphenyl)pyridine
(Cmpd 4p)

FIG. 30

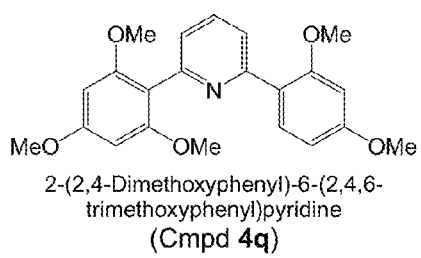

2-(2,4-Dimethoxyphenyl)-6-(2,4,6-trimethoxyphenyl)pyridine
(Cmpd 4q)

FIG. 31

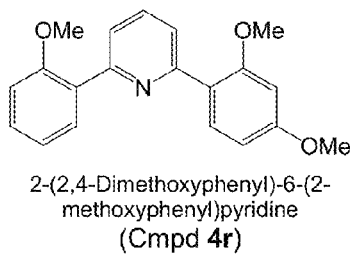

2-(2,4-Dimethoxyphenyl)-6-(2-methoxyphenyl)pyridine
(Cmpd 4r)

FIG. 32

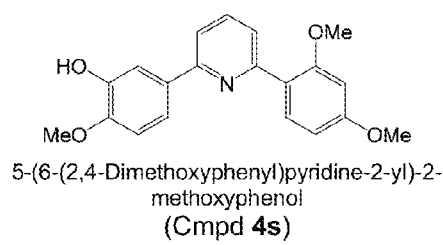

5-(6-(2,4-Dimethoxyphenyl)pyridine-2-yl)-2-methoxyphenol
(Cmpd 4s)

FIG. 33

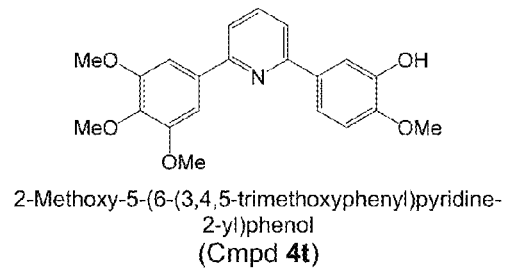

2-Methoxy-5-(6-(3,4,5-trimethoxyphenyl)pyridine-2-yl)phenol
(Cmpd 4t)

FIG. 34

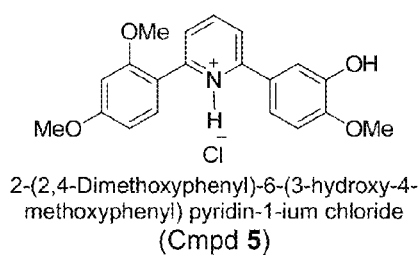

2-(2,4-Dimethoxyphenyl)-6-(3-hydroxy-4-methoxyphenyl) pyridin-1-ium chloride
(Cmpd 5)

FIG. 35

ANTI-VASCULATURE AND ANTI-TUBULIN COMBRETASTATIN ANALOGS FOR TREATMENT OF CANCER

CROSS-REFERENCE TO RELATED APPLICATIONS

This application is a National Stage entry of International Application No. PCT/US2015/022624, filed Mar. 26, 2015, which claims the benefit of U.S. Provisional Patent Application No. 61/972,749, filed 31 Mar. 31 2014, and which are hereby incorporated by reference in theft entirety.

STATEMENT REGARDING FEDERALLY SPONSORED RESEARCH OR DEVELOPMENT

This Invention was made with U.S. Government support under Contract No. 8G12MD007595 awarded by the National Institutes of Health. The Government has certain rights in this invention.

BACKGROUND

1. Field of the Disclosure

The present disclosure relates to new combretastatins analog compounds and their pharmaceutically acceptable salts; pharmaceutical compositions comprising the new combretastatin analog compounds, either alone or in combination with at least one additional therapeutic agent, with a pharmaceutically acceptable carrier; and uses of the new combretastatin analog compounds, either alone or in combination with at least one additional therapeutic agent, in the treatment of cancer, and in particular cancer presenting as metastatic tumors.

2. Description of Related Art

Inhibition of tubulin polymerization disrupts the formation of tumor vasculature, making the microtubule cytoskeleton an effective target for cancer chemotherapy [1-3]. Combretastatin A4 (CA-4) is the prototype of a large group of vascular disrupting agents that have been designed, synthesized, and tested in various biological models as potential therapeutic candidates for cancer treatment [4, 5]. CA-4 binds to the colchicine binding site of tubulin to block microtubule assembly, causing rapid vascular shutdown in the tumor and cell death [6]. The water-soluble phosphate prodrug form (CA-4P, also known as fosbretabulin) is in phase II/III clinical trials either alone or in combination with traditional chemotherapeutic agents or with radiotherapy [7-10]. Meanwhile, over the past two decades, numerous novel derivatives of CA-4 have been discovered to confer cytotoxic potency and anti-tubulin activity that are comparable to CA-4, significantly expanding the arsenal of vascular disrupting agents that could be further explored for clinical applications.

Modifications made on the two phenyl rings, for example, have led to hundreds of active compounds that possess desirable cytotoxicity while retaining varying degrees of anti-tubulin activities [11]. Most structural variations of the phenyl rings have occurred in the phenyl ring with hydroxyl and methoxy substitutions. These include various substituted phenyl rings [12] and other aromatic rings [13]. A fewer reports have attempted to modify the trimethoxy ring with mixed outcomes. For example, the m-methoxy group has been substituted by a fluoride [14] to yield a similarly potent compound. In another example, when the trimethoxy ring was replaced by a trimethyl ring [15], the cytotoxicity of the compound was significantly reduced but the anti-tubulin activity was largely retained. This suggests that it might be possible to achieve disruption of tumor vasculature with fewer cytotoxic side effects.

Modifications of the double bond have also led to diverse structural variations that remain viable as cytotoxic and anti-tubulin compounds. The olefinic bond is believed to be critical in placing the two phenyl rings at an appropriate distance and giving the molecule the right dihedral angle to maximize the interaction with the target. As such, replacement of the double bond by rings that facilitate a cis-locked configuration has proven to be effective in retaining both cytotoxicity and anti-tubulin activity [16-18]. Indeed, this strategy has led to the discovery of perhaps more active CA-4 analogs than any other types of structural modifications. On the other hand, the observation that two-carbon linkers are the optimal length of the bridge between the two phenyl rings has somewhat limited the effort to explore this strategy of modifications. However, there have been some encouraging exceptions. For example, when the methylene bridge is replaced by a carbonyl group, the resulting analog, phenstatin, actually retained much of the antitubulin activity [19]. Increasing the bridge length to three carbons such as a chalcone-like linker, have been reported to strongly inhibit tubulin polymerization as well as cell survival [20].

Despite the intense interest and the large number of potent derivatives that have been discovered in the therapeutic application of CA-4 and related derivatives targeting the colchicine-binding site of tubulin, none of these inhibitors has reached the clinical stage. Thus there remains an urgent need in developing CA-4 analogs with improved pharmacological properties for eventual acceptance in the clinic.

The present disclosure concerns the design, synthesis, and biological evaluation of a series of pyridine-linked CA-4 analogs (Formula I) in which the distance between the two phenyl rings is configured to be three or four atoms, i.e., meta- or para- to each other. Pyridine has been introduced to replace the cis-double bond between the A ring and B ring [21]. However, it was previously found that while the pyridine A4 derivatives retained some cytotoxicity, the anti-tubulin activities were largely lost. In this disclosure, we show that cytotoxicity and antitubulin activities comparable to CA-4 can be obtained with bridge length fixed at three atoms (including the pyridine nitrogen) if substitutions on one or both of the phenyl rings are optimized. Here we describe the synthesis of 34 pyridine-bridged CA-4 analogs that were tested for their ability to block tubulin polymerization as well as their cytotoxicity to several lines of human cancer cells. Molecular modeling was also performed to better understand the structural requirements for the pyridine-linked CA-4 analogs to retain antimitotic potency.

BRIEF SUMMARY OF THE INVENTION

To overcome the shortcomings in the art and to provide compounds suitable for the treatment of cellular proliferative diseases, we designed and synthesized a series of pyridine-linked CA-4 analogs (Formula I) in which the distance between the two phenyl rings is configured to be three or four atoms, i.e., meta- or para- to each other. We then evaluated the in vitro efficacies of these pyridine-linked CA-4 analogs in suppressing cell mitosis via inhibiting tubulin polymerization, in two models of invasive and metastatic cancer cell lines. We further evaluated the in vivo anti-angiogenesis of the most potent compounds using a Chick embryo chorioallantoic membrane (CAM) assay. Our results demonstrate the potential utility of the most potent CA-4 analogs as anti-tubulin, anti-proliferation, and anti-angiogenesis therapeutic agents for the treatment of cellular proliferative diseases.

Thus, in one aspect, the present disclosure relates to CA-4 analog compounds and their pharmaceutically acceptable salts; pharmaceutical compositions comprising the new CA-4 analog compounds, either alone or in combination with at least one additional therapeutic agent, with a pharmaceutically acceptable carrier; and uses of the new CA-4 analog compounds, either alone or in combination with at least one additional therapeutic agent, in the prophylaxis or treatment of cellular proliferative diseases, such as cancer, and in particular cancer presenting as metastatic tumors.

In another embodiment, the disclosure relates to pyridine-linked CA-4 analogs that have been discovered to have potent inhibitory effects on cancer cell growth and proliferation, with $IC_{50}$ values in the subnanomolar range. Thus, these CA-4 analogs can be useful in the treatment of metastatic tumors by disrupting the formation of tumor vasculature.

In accordance with another embodiment of the disclosure, methods of manufacturing the disclosed pyridine-linked CA-4 analog compounds are presented.

Another embodiment of the present disclosure relates to methods of using the pyridine-linked CA-4 analogs for the treatment of particular cancers, including breast cancer, and cancer cells that are invasive in nature.

Further, embodiments of the present disclosure may be utilized to treat a wide variety of cancers. For example, particular embodiments of the disclosure can be utilized in the treatment of the following carcinomas: Ovarian carcinoma (serous cystadenocarcinoma, mucinous cystadenocarcinoma, endometrioid carcinoma), Ovarian granulosa cell tumor, Fallopian tube adenocarcinoma, Peritoneal carcinoma, Uterine (endometrial) adenocarcinoma, sarcomatoid carcinoma, Cervical squamous cell carcinoma, Endocervical adenocarcinoma, Vulvar carcinoma, Breast carcinoma, primary and metastatic (ductal carcinoma, mucinous carcinoma, lobular carcinoma, malignant phyllodes tumor), Head and neck carcinoma, Oral cavity carcinoma including tongue, primary and metastatic, Esophageal carcinoma, squamous cell carcinoma and adenocarcinoma, Gastric adenocarcinoma, malignant lymphoma, GIST, Primary small bowel carcinoma, Colonic adenocarcinoma, primary and metastatic (adenocarcinoma, mucinous carcinoma, large cell neuroendocrine carcinoma, colloid carcinoma), Appendiceal adenocarcinoma, Colorectal carcinoma, Rectal carcinoma, Anal carcinoma (squamous, basaloid), Carcinoid tumors, primary and metastatic (appendix, small bowel, colon), Pancreatic carcinoma, Liver carcinoma (hepatocellular carcinoma, cholangiocarcinoma), Metastatic carcinoma to the liver, Lung cancer, primary and metastatic (squamous cell, adenocarcinoma, adenosquamous carcinoma, giant cell carcinoma, nonsmall cell carcinoma, NSCLC, small cell carcinoma neuroendocrine carcinoma, large cell carcinoma, bronchoalveolar carcinoma), Renal cell (kidney) carcinoma, primary and metastaic, Urinary bladder carcinoma, primary and metastatic, Prostatic adenocarcinoma, primary and metastatic, Brain tumors, primary and metastatic (glioblastoma, multiforme, cerebral neuroectodermal malignant tumor, neuroectodermal tumor, oligodendroglioma, malignant astrocytoma), Skin tumors (malignant melanoma, sebaceous cell carcinoma), Thyroid carcinoma (papillary and follicular), Thymic carcinoma, Shenoidal carcinoma, Carcinoma of unknown Primary, Neuroendocrine carcinoma, Testicular malignancies (seminoma, embryonal carcinoma, malignant mixed tumors), and others.

In another embodiment, the CA-4 analogs of the present disclosure can be used to treat the following malignant lymphomas, for example: Large cell malignant lymphoma, Small cell lymphoma, Mixed large and small cell lymphoma, Malt lymphoma, Non Hodgkin malignant lymphoma, T cell malignant lymphoma, and others.

Further still, embodiments of the disclosure may use the CA-4 analogs to treat the following leukemias, for example: AML-acute myelogenous leukemia, ALL-acute lymphoblastic leukemia, Chronic lymphocytic leukemia, Multiple myeloma, Myelodysplastic syndromes-MDS, MDS with myelofibrosis, Waldenstrom's macroglobulinemia, and others.

Also, sarcomas such as the following may be treated with embodiments of the presently disclosed CA-4 analogs: Leimyosarcoma (uterine sarcoma), GIST-gastrointestinal stromal tumor, primary and metastatic (stomach, small bowel, Colon), Liposarcoma, Myxoid sarcoma, Chondrosarcoma, Osteosarcoma, Ewings sarcoma/PNET, Neuroblastoma, Malignant peripheral nerve sheath tumor, Spindle cell carcinoma, Embryonal rhabdomyosarcoma, Mesothelioma, and others.

Thus, it can easily be recognized that the presently disclosed CA-4 analog compounds and their pharmaceutically acceptable salts- or pharmaceutical compositions comprising the new CA-4 analog compounds, either alone or in combination with at least one additional therapeutic agent, with a pharmaceutically acceptable carrier—are useful in the treatment of all types of cellular proliferative diseases, such as the multitude of cancers aforementioned.

It is a further object of the disclosure to provide a composition comprising one or more of the disclosed CA-4 compounds, used in combination with one or more of an existing chemotherapeutic agent, for minimizing or delaying tumor metastasis. In this aspect, the CA-4 analogs used in combination with a known chemotherapeutic agent, will produce beneficial anti-metastatic compositions and treatments that demonstrate superior efficacy when compared to treatments utilizing only the known chemotherapeutic agent.

Another embodiment of this disclosure is a kit, comprising a composition containing one or more of the disclosed CA-4 compounds, used alone or in combination with an existing chemotherapeutic agent, and a delivery mechanism. The delivery mechanism would be any type of device or system known to those of skill in the art to be suitable for the administration of the composition to a human or animal subject, e.g. syringes, intravenous bags and assemblages, etc. The kit would be useful for minimizing the time and inefficiencies that are created by doctors having to individually assemble the components necessary for delivering a treatment to a patient. Consequently, the kit embodiment of the disclosure could be utilized as an off the shelf, or prepackaged, treatment protocol. These types of prepackaged drug delivery systems are of particular importance in understaffed hospitals or developing countries, in which there is not a sufficient level of medical expertise available to accurately determine the appropriate dosage of a composition comprising the pyridine-bridged analog of CA-4 on a fast and consistent basis. The kits therefore provide a fast and accurate method by which to utilize the disclosed pyridine-bridged analog of CA-4.

In other embodiments, the particular CA-4 analog can be any of the individually listed compounds recited in the below "Compound List and Identifications" section. Furthermore, any pharmaceutically acceptable salt of the individually listed compounds are also part of the present disclosure. Further still, as aforementioned, a composition comprising any combination of the below listed pyridine-bridged analogs of CA-4 is also a part of the present disclosure. Said composition can include any pharmaceutically acceptable carrier, as well as a further therapeutic agent, for example a known chemotherapeutic agent.

In another aspect, the present disclosure provides methods for treating cellular proliferative diseases, such as cancer, in a human or animal subject in need of such treatment, comprising administering to said subject an amount of a CA-4 analog, selected from the below "Compound List and Identifications," which is effective to reduce or prevent cellular proliferation in the subject. Said method may also include administering any of the listed CA-4 analog in a composition, which comprises a pharmaceutically acceptable carrier, as well as a further therapeutic agent. The therapeutic agent administered along with one or more of the disclosed CA-4 analogs may be any agent known in the art to be beneficial for the treatment of cancer, such as chemotherapeutic agents, radiation, immunotherapeutic agents, etc.

In one aspect, the present disclosure provides compounds of Formula (I):

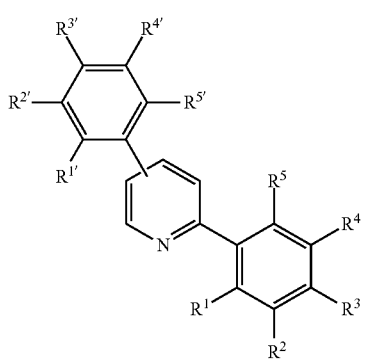

wherein
$R^1$, $R^2$, $R^3$, $R^4$, and $R^5$ is H, hydroxyl, methoxy, or ethoxy, and in any combinations thereof;
and wherein
$R^{1\prime}$, $R^{2\prime}$, $R^{3\prime}$, $R^{4\prime}$ and $R^{5\prime}$ is H, hydroxyl, methoxy, or ethoxy, and in any combinations thereof.

COMPOUND LIST AND IDENTIFICATIONS

Compounds 2-5 are referred to collectively as pyridine containing pyridine-bridged analogs of CA-4 with strong cytotoxicity and anti-tubulin agents throughout the disclosure.

While certain novel features of this disclosure shown and described below are pointed out in the annexed claims, the disclosure is not intended to be limited to the details specified, since a person of ordinary skill in the relevant art will understand that various omissions, modifications, substitutions and changes in the forms and details of the disclosure illustrated, and in its operation, may be made without departing in any way from the spirit of the present disclosure. No feature of the disclosure is critical or essential unless it is expressly stated as being critical or essential.

BRIEF DESCRIPTION OF THE DRAWINGS

These and other features, aspects, and advantages of embodiments of the present disclosure will become better understood with regard to the following description, claims, and accompanying drawings, in which:

FIG. 1 shows 2-Bromo-6-(3,4,5-trimethoxyphenyl)pyridine, which is referred to as compound 2a, and represented by the number 2a.

FIG. 7 shows 2,6-Bis(3,4,5-trimethoxyphenyl)pyridine, which is referred to as compound 3a, and represented by the number 3a.

FIG. 15 shows 4-(6-(3,4,5-trimethoxyphenyl)pyridin-2-yl)phenol, which is referred to as compound 4a, and represented by the number 4a.

FIG. 16 shows 4-(6-(3,4-dimethoxyphenyl)pyridin-2-yl)phenol, which is referred to as compound 4b, and represented by the number 4b.

FIG. 17 shows 2-(3,4-Dimethoxyphenyl)-6-(3,4,5-trimethoxyphenyl)pyrdine, which is referred to as compound 4c, and represented by the number 4c.

FIG. 18 shows 2-(3,4-Dimethoxyphenyl)-6-(4-methoxyphenyl)pyridine, which is referred to as compound 4d, and represented by the number 4d.

FIG. 19 shows 2-(2,4-Dimethoxyphenyl)-6-(3,4-dimethoxyphenyl)pyrdine, which is referred to as compound 4e, and represented by the number 4e.

FIG. 20 shows 2-(4-Methoxyphenyl)-6-(3,4,5-trimethoxyphenyl)pyridine, which is referred to as compound 4f, and represented by the number 4f.

FIG. 21 shows 2-(2,4-Dimethoxyphenyl)-6-(3,4,5-trimethoxyphenyl)pyrdine, which is referred to as compound 4g, and represented by the number 4g.

FIG. 22 shows 2-(2,4-Dimethoxyphenyl)-6-(4-methoxyphenyl)pyrdine, which is referred to as compound 4h, and represented by the number 4h.

FIG. 29 shows 2-(2,4-Dimethoxyphenyl)-6-(2,6-dimethoxyphenyl)pyridine, which is referred to as compound 4o and represented by the number 4o.

FIG. 30 shows 2-(2,4-Dimethoxyphenyl)-6-(3-methoxyphenyl)pyridine, which is referred to as compound 4p and represented by the number 4p.

FIG. 31 shows 2-(2,4-Dimethoxyphenyl)-6-(2,4,6-trimethoxyphenyl)pyridine, which is referred to as compound 4q and represented by the number 4q.

FIG. 32 shows 2-(2,4-Dimethoxyphenyl)-6-(2-methoxyphenyl)pyridine, which is referred to as compound 4r and represented by the number 4r.

FIG. 33 shows 5-(6-(2,4-Dimethoxyphenyl)pyridine-2-yl)-2-methoxyphenol, which is referred to as compound 4s and represented by the number 4s.

FIG. 34 shows 2-Methoxy-5-(6-(3,4,5-trimethoxyphenyl) pyridine-2-yl)phenol, which is referred to as compound 4t and represented by the number 4t.

FIG. 35 shows 2-(2,4-Dimethoxyphenyl)-6-(3-hydroxy-4-methoxyphenyl) pyridin-1-ium chloride, which is referred to as compound 5 and represented by the number 5.

DETAILED DESCRIPTION

Figure 1:
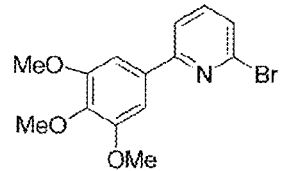
Figure 2:
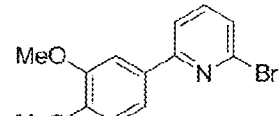
FIG. 2 shows 2-Bromo-6-(3,4-dimethoxyphenyl)pyridine, which is referred to as compound 2b, and represented by the number 2b.
Figure 3:
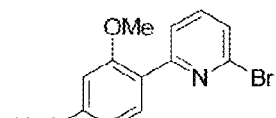
FIG. 3 shows 2-Bromo-6-(2,4-dimethoxyphenyl)pyridine, which is referred to as compound 2c, and represented by the number 2c
Figure 4:
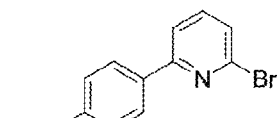
FIG. 4 shows 2-Bromo-6-(4-methoxyphenyl)pyridine, which is referred to as compound 2d, and represented by the number 2d.
Figure 5:
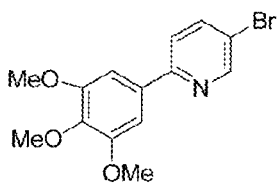
FIG. 5 shows 5-Bromo-2-(3,4,5-trimethoxyphenyl)pyridine, which is referred to as compound 2e, and represented by the number 2e.
Figure 6:
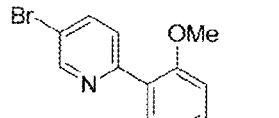
FIG. 6 shows 5-Bromo-2-(2,4-dimethoxyphenyl)pyridine, which is referred to as compound 2f, and represented by the number 2f.
Figure 7:
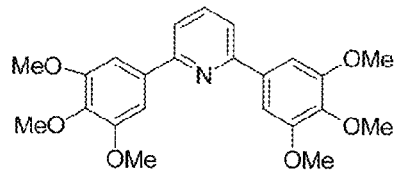
Figure 8:
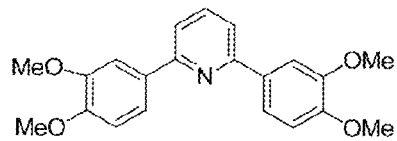
FIG. 8 shows 2,6-Bis(3,4-dimethoxyphenyl)pyridine, which is referred to as compound 3b, and represented by the number 3b.
Figure 9:
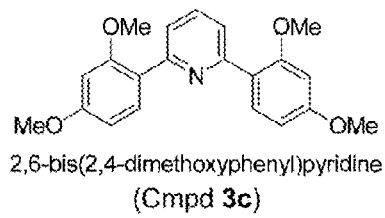
FIG. 9 shows 2,6-Bis(2,4-dimethoxyphenyl)pyridine, which is referred to as compound 3c, and represented by the number 3c.
Figure 10:
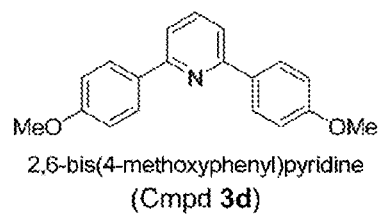
FIG. 10 shows 2,6-Bis(4-methoxyphenyl)pyridine, which is referred to as compound 3d, and represented by the number 3d.
Figure 11:
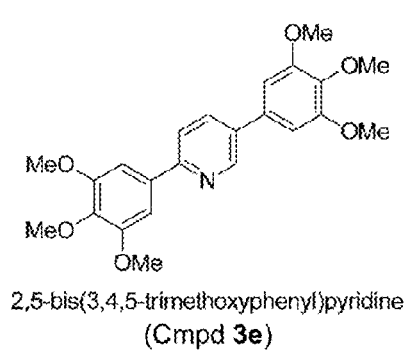
FIG. 11 shows 2,5-Bis(3,4,5-trimethoxyphenyl)pyridine, which is referred to as compound 3e, and represented by the number 3e.
Figure 12:
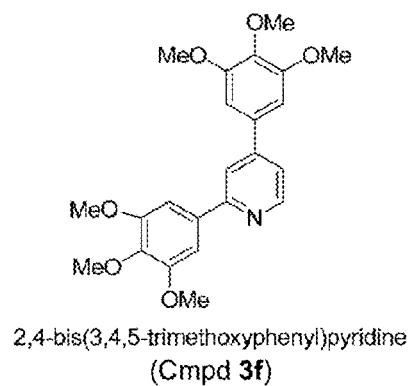
FIG. 12 shows 2,4-Bis(3,4,5-trimethoxyphenyl)pyridine, which is referred to as compound 3f, and represented by the number 3f.
Figure 13:
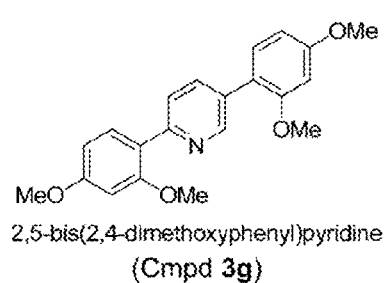
FIG. 13 shows 2,5-Bis(2,4-dimethoxyphenyl)pyridine, which is referred to as compound 3g, and represented by the number 3g.
Figure 14:
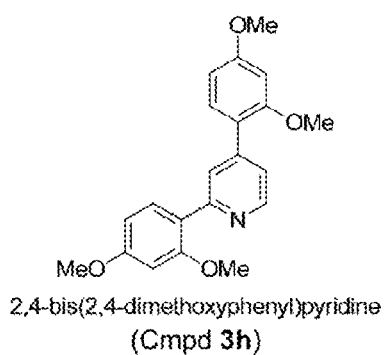
FIG. 14 shows 2,4-Bis(2,4-dimethoxyphenyl)pyridine, which is referred to as compound 3h, and represented by the number 3h.
Figure 23:
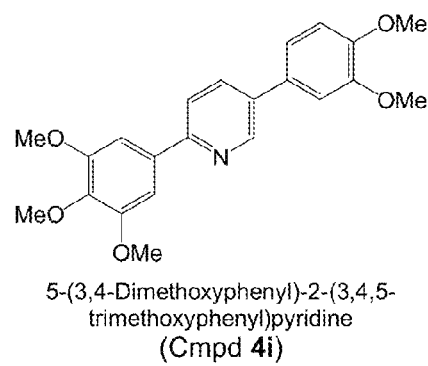
FIG. 23 shows 5-(3,4-Dimethoxyphenyl)-2-(3,4,5-trimethoxyphenyl)pyrdine, which is referred to as compound 4i, and represented by the number 4i.
Figure 24:
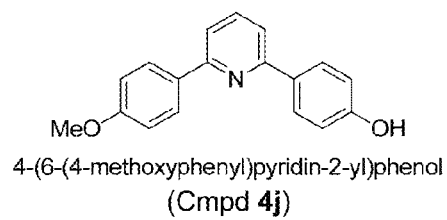
FIG. 24 shows 4-(6-(4-Methoxyphenyl)pyridine-2-yl) phenol, which is referred to as compound 4j and represented by the number 4j.
Figure 25:
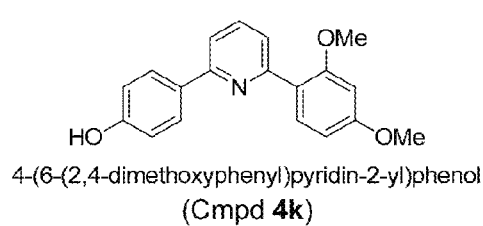
FIG. 25 shows 4-(6-(2,4-Dimethoxyphenyl)pyridine-2-yl)phenol, which is referred to as compound 4k and represented by the number 4k.
Figure 26:
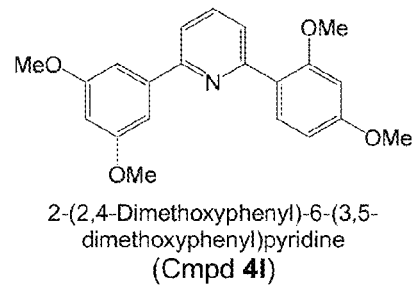
FIG. 26 shows 2-(2,4-Dimethoxyphenyl)-6-(3,5-dimethoxyphenyl)pyridine, which is referred to as compound 4l and represented by the number 4l.
Figure 27:
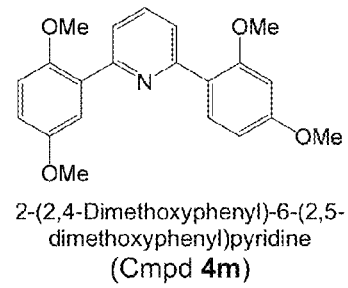
FIG. 27 shows 2-(2,4-Dimethoxyphenyl)-6-(2,5-dimethoxyphenyl)pyridine, which is referred to as compound 4m and represented by the number 4m.
Figure 28:
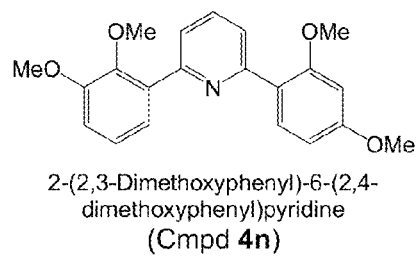
FIG. 28 shows 2-(2,3-Dimethoxyphenyl)-6-(2,4-dimethoxyphenyl)pyridine, which is referred to as compound 4n and represented by the number 4n.
Figure 36:
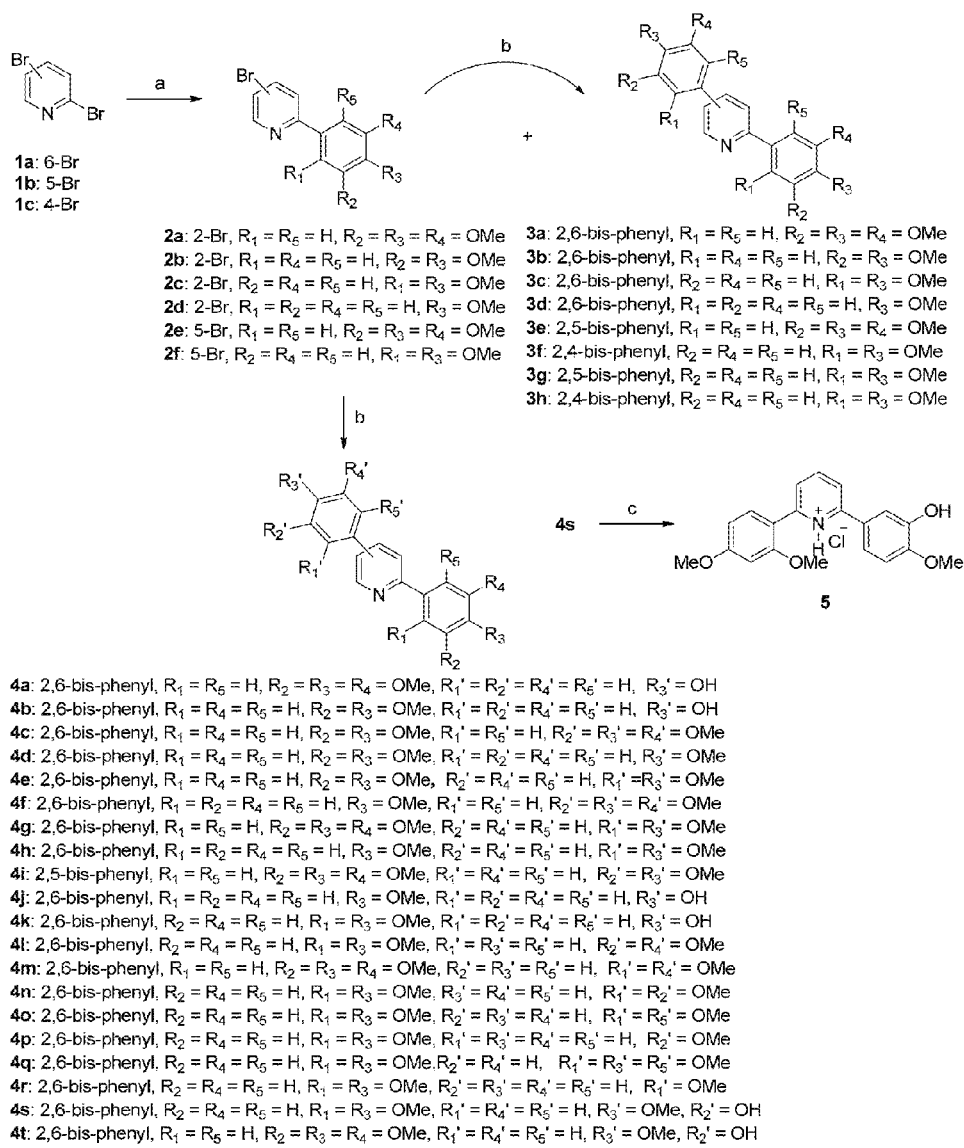
FIG. 36 shows the synthesis of pyridine-bridged analogs of combrestastatin-A4. Reagents and conditions: (a) $RB(OH)_2$, toluene-$H_2O$ (4:1), $Na_2CO_3$, 80° C.; (b) RB(OH)$_2$, toluene-$H_2O$ (4:1), $Na_2CO_3$, 120° C.; (c) HCl in ether, rt.

Detailed descriptions of one or more preferred embodiments are provided herein. It is to be understood, however, that the present disclosure may be embodied in various forms. Therefore, specific details disclosed herein are not to be interpreted as limiting, but rather as a basis for the claims and as a representative basis for teaching one skilled in the art to employ the present disclosure in any appropriate manner.

One aspect of the present disclosure describes the synthesis of pyridine-bridged analogs of CA-4. Another embodiment of the disclosure describes the potent cytotoxicity on cancer cells exhibited by the disclosed pyridine-bridged analogs of CA-4.

To determine if these analogs have cytotoxicity in different cancer cell lines, we performed antiproliferative assays in human breast adenocarcinoma (MDA-MB-231), human nonsmall cell lung carcinoma (A549) and human cervix carcinoma (HeLa) cells for all synthetic analogs. The most potent analogs, 4h, 4s, and 4t were also tested to determine antimicrotubule effect in HeLa and MDA-MB-231 cells by tubulin polymerization assays. We next performed flow cytometry assays on HeLa and MDA-MB-231 cells treated with the compounds to investigate the effect of 4h and 4s on cell cycle arrest. Chick embryo chorioallantoic membrane (CAM) assay was used to further investigate the anti-angiogenesis properties of 4h, 4s, and 4t.

As used herein, the term "minimize" or "reduce", or derivatives thereof, include a complete or partial inhibition of a specified biological effect (which is apparent from the context in which the terms "minimize" or "reduce" are used).

EXAMPLE 1

Synthesis of Pyridine-bridged CA-4 Analogs

General procedure for synthesis of compounds 2 and 3: The mixture of the dibromopyridines 1a-c (11.8 g, 0.05 mol), the phenyl boronic acids (0.075 mol), sodium carbonate (15.9 g, 0.15 mol) and $PdCl_2$(dppf) (0.40 g, 0.5 mmol) in toluene-ethanol (4:1, 100 mL) was stirred at 80° C. until the reaction finished (about 3 days~4 days). After cooling down to room temperature, the reaction mixture was filtered through celite and the filtrate was concentrated. The residue crude was purified to afford products 2 and 3 (minor) by flash column chromatography on silica gel with hexane-ethyl acetate (9:1) as eluent.

2-Bromo-6-(3,4,5-trimethoxyphenyl)pyridine (2a): 7.0 g, Yield: 43%. Solid, mp 100-102° C. $^1$H-NMR (CDCl$_3$, 300 Hz): 7.64-7.55 (2H, m), 7.39 (1H, d, J=7.2 Hz), 7.21 (2H, s), 3.96 (6H, s), 3.90 (3H, s). $^{13}$C-NMR (CDCl$_3$, 75 Hz): 158.3, 153.5, 142.0, 139.6, 139.0, 133.3, 126.2, 118.9, 104.3, 61.0, 56.3. MS-EI: 323, 325 (M$^+$). HRMS (ESI(+)): Calcd. for $C_{14}H_{15}BrNO_3$ (M+H): 324.0235, 326.0215. Found: 324.0225, 326.0204.

2-Bromo-6-(3,4-dimethoxyphenyl)pyridine (2b): 6.3 g, Yield: 43%. Solid, mp 78-80° C. $^1$H-NMR (CDCl$_3$, 300 Hz): 7.64-7.61 (2H, m), 7.56 (1H, d, J=7.8 Hz), 7.51 (1H, dd, J=2.1 and 8.4 Hz), 7.35 (1H, dd, J=0.9 and 7.8 Hz), 6.93 (1H, d, J=8.4 Hz), 3.99 (3H, s), 3.93 (3H, s). $^{13}$C-NMR (CDCl$_3$, 75 Hz): 158.2, 150.4, 149.2, 142.0, 138.9, 130.5, 125.6, 119.6, 118.3, 110.9, 109.9, 56.0, 55.9. MS-EI: 293, 295 (M$^+$). HRMS (ESI(+)): Calcd. for $C_{13}H_{13}BrNO_2$(M+H): 294.0129, 296.0109. Found: 294.0123, 296.0104.

2-Bromo-6-(2,4-dimethoxyphenyl)pyridine (2c): 11.0 g, Yield: 75%. Solid, mp 48-50° C. $^1$H-NMR (CDCl$_3$, 300 Hz): 7.86 (2H, m), 7.50 (1H, m), 7.30 (1H, d, J=7.8 Hz), 6.60 (1H, dd, J=2.1 and 8.4 Hz), 6.52 (1H, d, J=2.1 Hz), 3.85 (6H, s). $^{13}$C-NMR (CDCl$_3$, 75 Hz): 161.8, 158.3, 156.7, 141.2, 138.0, 132.3, 127.0, 125.1, 123.2, 105.2, 98.7, 55.5, 55.4. MS-EI: 293, 295 (M$^+$). HRMS (ESI(+)): Calcd. for $C_{13}H_{13}BrNO_2$(M+H): 294.0129, 296.0109. Found: 294.0126, 296.0100.

2-Bromo-6-(4-methoxyphenyl)pyridine (2d): 8.1 g, Yield: 62%. Solid, mp 99-100° C. $^1$H-NMR (CDCl$_3$, 300 Hz): 7.95 (2H, d, J=9.0 Hz), 7.61 (1H, dd, J=0.9 and 7.8 Hz), 7.55 (1H, m), 7.34 (1H, dd, J=1.9 and 7.5 Hz), 6.98 (2H, d, J=9.0 Hz), 3.87 (3H, s). $^{13}$C-NMR (CDCl$_3$, 75 Hz): 160.9, 158.2, 142.0, 138.9, 130.2, 128.3, 125.4, 118.1, 114.1, 55.3. MS-EI: 263, 265 (M+). HRMS (ESI(+)): Calcd. for $C_{12}H_{11}BrNO$ (M+H): 264.0024, 266.0004. Found: 264.0011, 266.0000.

5-Bromo-2-(3,4,5-trimethoxyphenyl)pyridine (2e): 6.3 g, Yield: 39%. Solid, mp 49-50° C. $^1$H-NMR (CDCl$_3$, 300 Hz): 8.70 (1H, d, J=2.4 Hz), 7.85 (1H, dd, J=2.4 and 8.7 Hz), 7.58 (1H, d, J=8.4 Hz), 7.21 (2H, s), 3.96 (6H, s), 3.91 (3H, s). $^{13}$C-NMR (CDCl$_3$, 75 Hz): 155.4, 153.5, 150.5, 139.3, 139.2, 133.8, 121.4, 119.1, 103.9, 60.9, 56.2. MS-EI: 323, 325 (M+). HRMS (ESI(+)): Calcd. for $C_{14}H_{15}BrNO_3$ (M+H): 324.0235, 326.0215. Found: 324.0224, 326.0203.

5-Bromo-2-(2,4-dimethoxyphenyl)pyridine (2f): 7.2 g, Yield: 49%. Solid, mp 90-92° C. $^1$H-NMR (CDCl$_3$, 300 Hz): 8.70 (1H, m), 7.79-7.75 (3H, m), 6.61 (1H, dd, J=2.4 and 8.7 Hz), 6.55 (1H, d, J=2.4 Hz), 3.86 (3H, s), 3.85 (3H, s). $^{13}$C-NMR (CDCl$_3$, 75 Hz): 161.6, 158.1, 154.2, 150.1, 138.2, 131.8, 125.8, 120.7, 118.0, 105.1, 98.8, 55.6, 55.5. MS-EI: 293, 295 (M+). HRMS (ESI(+)): Calcd. for $C_{13}H_{13}BrNO_2$(M+H): 294.0129, 296.0109. Found: 294.0121, 296.0099.

2,6-Bis(3,4,5-trimethoxyphenyl)pyridine (3a): 0.4 g, Yield: 4%. Solid, mp 175-176° C. $^1$H-NMR (CDCl$_3$, 300 Hz): 7.81 (1H, m), 7.64 (2H, d, J=7.8 Hz), 7.41 (4H, s), 3.98 (12H, s), 3.92 (6H, s). $^{13}$C-NMR (CDCl$_3$, 75 Hz): 156.3, 153.5, 139.1, 137.5, 135.0, 118.3, 104.2, 61.1, 56.2. MS-EI: 411 (M+). HRMS (ESI(+)): Calcd. for $C_{23}H_{26}NO_6$ (M+H): 412.1760. Found: 412.1745.

2,6-Bis(3,4-dimethoxyphenyl)pyridine (3b): 2.4 g, Yield: 14%. Solid, mp 140-141° C. $^1$H-NMR (CDCl$_3$, 300 Hz): 7.84 (2H, d, J=1.8 Hz), 7.76 (1H, m), 7.65 (2H, dd, J=1.8 and 8.1 Hz), 7.60 (2H, d, J=7.8 Hz), 6.98 (2H, d, J=8.1 Hz), 4.02 (6H, s), 3.96 (6H, s). $^{13}$C-NMR (CDCl$_3$, 75 Hz): 156.2, 150.0, 149.1, 137.4, 132.5, 119.4, 117.5, 111.0, 110.0, 56.0, 55.9. MS-EI: 351 (M+). HRMS (ESI(+)): Calcd. for $C_{21}H_{22}NO_4$ (M+H): 352.1549. Found: 352.1538.

2,5-Bis(3,4,5-trimethoxyphenyl)pyridine (3e): 1.5 g, Yield: 7%. Solid, mp 176-177° C. $^1$H-NMR (CDCl$_3$, 300 Hz): 8.88 (1H, dd, J=0.9 and 2.4 Hz), 7.90 (1H, dd, J=2.4 and 8.1 Hz), 7.76 (1H, dd, J=0.9 and 8.4 Hz), 7.30 (2H, s), 6.81 (2H, s), 3.99 (6H, s), 3.95 (6H, s), 3.922 (3H, s), 3.915 (3H, s). $^{13}$C-NMR (CDCl$_3$, 75 Hz): 155.7, 153.7, 153.5, 147.8, 139.1, 138.2, 135.0, 134.5, 133.4, 120.0, 104.2, 103.9, 61.03, 61.00, 56.2. MS-EI: 411 (M+). HRMS (ESI(+)): Calcd. for $C_{23}H_{26}NO_6$(M+H): 412.1760. Found: 412.1744.

2,4-Bis(3,4,5-trimethoxyphenyl)pyridine (3f): 1.9 g, Yield: 9%. Solid, mp 116-118° C. $^1$H-NMR (CDCl$_3$, 300 Hz): 8.70 (1H, d, J=5.1 Hz), 7.79 (1H, s), 7.41 (1H, d, J=5.1 Hz), 7.26 (2H, s), 6.86 (2H, s), 3.98 (6H, s), 3.96 (6H, s), 3.93 (3H, s), 3.92 (3H, s). $^{13}$C-NMR (CDCl$_3$, 75 Hz): 157.7, 153.8, 153.6, 149.9, 149.7, 139.2, 139.1, 135.0, 134.4, 120.4, 118.8, 104.5, 104.4, 61.0, 60.9, 56.39, 56.35. MS-EI: 411 (M+). HRMS (ESI(+)): Calcd. for $C_{23}H_{26}NO_6$(M+H): 412.1760. Found: 412.1746.

2,5-Bis(2,4-dimethoxyphenyl)pyridine (3g): 6.2 g, Yield: 36%. Solid, mp 124-125° C. $^1$H-NMR (CDCl$_3$, 300 Hz): 8.79 (1H, m), 7.84-7.81 (3H, m), 7.30 (1H, d, J=8.1 Hz), 6.65-6.57 (4H, m), 3.68 (9H, s), 3.83 (3H, s). $^{13}$C-NMR (CDCl$_3$, 75 Hz): 161.1, 160.8, 158.1, 157.7, 153.5, 149.5, 136.3, 131.9, 131.3, 131.0, 123.8, 122.0, 120.0, 105.0, 104.8, 99.0, 98.8, 55.59, 55.53, 55.48, 55.45. MS-EI: 351 (M+). HRMS (ESI(+)): Calcd. for $C_{21}H_{22}NO_4$ (M+H): 352.1549. Found: 352.1538.

2,4-Bis(2,4-dimethoxyphenyl)pyridine (3h): 2.2 g, Yield: 12%. Solid, mp 95-97° C. $^1$H-NMR (CDCl$_3$, 300 Hz): 8.65 (d, J=5.1 Hz, 1H), 7.92 (dd, J=1.5 and 0.6 Hz, 1H), 7.77 (d, J=8.4 Hz, 1H), 7.36 (dd, J=5.1 and 1.5 Hz, 1H), 7.35 (d, J=8.1 Hz, 1H), 6.66-6.56 (m, 4H), 3.880 (s, 3H), 3.878 (s, 3H), 3.86 (s, 3H), 3.85 (s, 3H). $^{13}$C-NMR (CDCl$_3$, 75 Hz): 161.2, 161.1, 158.0, 157.8, 155.7, 148.8, 145.7, 132.0, 131.2, 125.1, 122.6, 121.8, 121.1, 104.9, 98.99, 98.87, 55.6, 55.5, 55.43, 55.41. MS-EI: 351 (M+). HRMS (ESI(+)): Calcd. for $C_{21}H_{22}NO_4$ (M+H): 352.1549. Found: 352.1537.

Procedure for synthesis of compounds 3d: The mixture of 2-bromo-6-(4-methoxyphenyl)pyridine 2d (1.3 g, 5 mmol), 4-methoxyphenyl boronic acids (1.1 g, 7.5 mol), sodium carbonate (1.6 g, 0.015 mol) and PdCl$_2$(dppf) (0.1 g, 0.1 mmol) in toluene-ethanol (4:1, 10 mL) was stirred overnight at 120° C. After cooling down to room temperature, the reaction mixture was filtered through celite and the filtrate was concentrated. The residue crude was purified to afford product 3d by flash column chromatography on silica gel with hexane-ethyl acetate (9:1) as eluent.

2,6-Bis(4-methoxyphenyl)pyridine (3d): 1.3 g, Yield: 89%. Solid, mp 156-158° C. $^1$H-NMR (CDCl$_3$, 300 Hz): 8.10 (4H, d, J=9.0 Hz), 7.74 (1H, m), 7.57 (2H, dd, J=0.6 and 7.5 Hz), 7.01 (4H, d, J=9.0 Hz), 3.87 (6H, s). $^{13}$C-NMR (CDCl$_3$, 75 Hz): 160.4, 156.3, 137.3, 132.3, 128.2, 117.2, 114.0, 55.4. MS-EI: 291 (M+). HRMS (ESI(+)): Calcd. for $C_{19}H_{18}NO_2$ (M+H): 292.1337. Found: 292.1327.

Procedure for synthesis of compounds 3c: The mixture of 2,6-dibromopyridines 1a (5.9 g, 0.025 mol), 2,4-dimethoxyphenyl boronic acids (13.7 g, 0.075 mol), sodium carbonate (15.9 g, 0.15 mol) and PdCl$_2$(dppf) (0.20 g, 0.25 mmol) in toluene-ethanol (4:1, 50 mL) was stirred overnight at 120° C. After cooling down to room temperature, the reaction mixture was filtered through celite and the filtrate was concentrated. The residue crude was purified to afford product 3c by flash column chromatography on silica gel with hexane-ethyl acetate (9:1) as eluent.

2,6-Bis(2,4-dimethoxyphenyl)pyridine (3c): 8.0 g, Yield: 92%. Solid, mp 113-114° C. $^1$H-NMR (CDCl$_3$, 300 Hz): 7.93 (2H, d, J=8.4 Hz), 7.73-7.62 (3H, m), 6.62 (2H, dd, J=2.1 and 8.4 Hz), 6.55 (2H, d, J=2.1 Hz), 3.85 (12H, s). $^{13}$C-NMR (CDCl$_3$, 75 Hz): 161.1, 158.3, 155.0, 135.2, 132.3, 122.7, 122.2, 105.1, 98.8, 55.6, 55.5. MS-EI: 351 (M+). HRMS (ESI(+)): Calcd. for $C_{21}H_{22}NO_4$ (M+H): 352.1549. Found: 352.1537.

General procedure for synthesis of compounds 4: The mixture of the monobromopyridines 2a-f (3 mmol), the phenyl boronic acids (4 mmol), sodium carbonate (0.5 g, 5 mmol) and PdCl$_2$(dppf) (0.1 g, 0.1 mmol) in toluene-ethanol (4:1, 100 mL) was stirred overnight at 120° C. After cooling down to room temperature, the reaction was quenched with saturated ammonium chloride solution; the organic layer was separated and extracted with ethyl acetate. The combined organic solution was dried over MgSO$_4$, filtered and concentrated. The residue crude was purified to afford products 4 by flash column chromatography on silica gel with hexane-ethyl acetate as eluent.

4-(6-(3,4,5-Trimethoxyphenyl)pyridin-2-yl)phenol (4a): Eluent: hexane-ethyl acetate (7:3). 0.42 g, Yield: 41%. Solid, mp 92-94° C. (d). $^1$H-NMR (DMSO-d6, 300 Hz): 9.79 (1H, s), 8.05 (2H, d, J=8.1 Hz), 7.85-7.62 (3H, m), 7.47 (2H, s), 6.90 (2H, d, J=8.1 Hz), 3.90 (6H, s), 3.72 (3H, s). $^{13}$C-NMR (DMSO-d6, 75 Hz): 158.6, 155.5, 155.1, 153.1, 138.5, 137.9, 134.5, 129.6, 128.0, 117.7, 117.5, 115.5, 104.0, 60.1, 56.0. MS-EI: 337 (M+). HRMS (ESI(+)): Calcd. for $C_{20}H_{20}NO_4$(M+H): 338.1392. Found: 338.1390.

4-(6-(3,4-Dimethoxyphenyl)pyridin-2-yl)phenol (4b): Eluent: hexane-ethyl acetate (7:3). 0.37 g, Yield: 40%. Solid, mp 70-72° C. $^1$H-NMR (DMSO-d6, 300 Hz): 9.78 (1H, s), 8.05 (2H, d, J=8.1 Hz), 7.85-7.71 (5H, m), 7.06 (1H, m), 6.90 (2H, d, J=8.1 Hz), 3.88 (3H, s), 3.82 (3H, s). $^{13}$C-NMR (DMSO-d6, 75 Hz): 158.5, 155.5, 155.1, 149.8, 148.8, 137.8, 131.6, 129.7, 128.0, 119.2, 117.1, 116.9, 115.5, 111.7, 110.0, 55.5. MS-EI: 307 (M$^+$). HRMS (ESI(+)): Calcd. for $C_{19}H_{18}NO_3$ (M+H): 308.1285. Found: 308.1278.

2-(3,4-Dimethoxyphenyl)-6-(3,4,5-trimethoxyphenyl)pyridine (4c): Eluent: hexane-ethyl acetate (8:2). 0.91 g, Yield: 80%. Solid, mp 107-108° C. $^1$H-NMR (CDCl$_3$, 300 Hz): 7.83 (1H, d, J=1.8 Hz), 7.78 (1H, m), 7.67-7.59 (3H, m), 7.40 (2H, s), 6.98 (1H, d, J=8.4 Hz), 4.01 (3H, s), 3.98 (6H, s), 3.96 (3H, s), 3.92 (3H, s). $^{13}$C-NMR (CDCl$_3$, 75 Hz): 156.2, 153.4, 150.0, 149.1, 139.0, 137.4, 135.2, 132.3, 119.4, 117.8, 111.0, 109.9, 104.1, 61.0, 56.1, 56.0, 55.8. MS-EI: 381 (M$^+$). HRMS (ESI(+)): Calcd. for $C_{22}H_{24}NO_5$ (M+H): 382.1654. Found: 382.1639.

2-(3,4-Dimethoxyphenyl)-6-(4-methoxyphenyl)pyridine (4d): Eluent: hexane-ethyl acetate (8:2). 0.94 g, Yield: 97%. Solid, mp 114-115° C. $^1$H-NMR (CDCl$_3$, 300 Hz): 8.10 (2H, d, J=9.0 Hz), 7.81 (1H, d, J=1.8 Hz), 7.75 (1H, m), 7.66 (1H, dd, J=1.8 and 8.4 Hz), 7.58 (2H, d, J=7.8 Hz), 7.02 (2H, d, J=9.0 Hz), 6.97 (1H, d, J=8.4 Hz), 4.02 (3H, s), 3.95 (3H, s), 3.88 (3H, s). $^{13}$C-NMR (CDCl$_3$, 75 Hz): 160.4, 156.3, 149.9, 149.1, 137.3, 132.6, 132.2, 128.2, 119.5, 117.4, 114.0, 111.0, 110.0, 55.9, 55.3. MS-EI: 321 (M$^+$). HRMS (ESI(+)): Calcd. for $C_{20}H_{20}NO_3$ (M+H): 322.1443. Found: 322.1432.

2-(2,4-Dimethoxyphenyl)-6-(3,4-dimethoxyphenyl)pyridine (4e): Eluent hexane-ethyl acetate (8:2). 1.0 g, Yield: 95%. Solid, mp 100-101° C. $^1$H-NMR (CDCl$_3$, 300 Hz): 8.02 (1H, d, J=8.7 Hz), 7.80-7.78 (2H, m), 7.72 (1H, m), 7.63 (1H, dd, J=2.1 and 8.4 Hz), 7.58 (1H, dd, J=1.2 and 7.5 Hz), 6.97 (1H, d, J=8.4 Hz), 6.68 (1H, dd, J=2.4 and 8.7 Hz), 6.59 (1H, d, J=2.4 Hz), 4.01 (3H, s), 3.96 (3H, s), 3.89 (6H, s). $^{13}$C-NMR (CDCl$_3$, 75 Hz): 161.3, 158.4, 156.2, 155.0, 149.7, 149.1, 136.2, 132.9, 132.2, 122.5, 122.3, 119.4, 117.2, 110.9, 110.1, 105.1, 98.8, 55.9, 55.6, 55.4. MS-EI: 351 (M$^+$). HRMS (ESI(+)): Calcd. for $C_{21}H_{22}NO_4$ (M+H): 352.1549. Found: 352.1537.

2-(4-Methoxyphenyl)-6-(3,4,5-trimethoxyphenyl)pyridine (4f): Eluent: hexane-ethyl acetate (8:2). 0.74 g, Yield: 70%. Solid, mp 112-114° C. $^1$H-NMR (CDCl$_3$, 300 Hz): 8.09 (2H, d, J=9.0 Hz), 7.77 (1H, m), 7.63-7.56 (2H, m), 7.37 (2H, s), 7.02 (2H, d, J=9.0 Hz), 3.99 (6H, s), 3.92 (3H, s), 3.88 (3H, s). $^{13}$C-NMR (CDCl$_3$, 75 Hz): 160.5, 156.4, 153.4, 139.0, 137.4, 135.4, 132.0, 128.2, 117.8, 114.0, 104.2, 60.9, 56.2, 55.3. MS-EI: 351 (M$^+$). HRMS (ESI(+)): Calcd. for $C_{21}H_{22}NO_4$ (M+H): 352.1549. Found: 352.1538.

2-(2,4-Dimethoxyphenyl)-6-(3,4,5-trimethoxyphenyl)pyridine (4g): Eluent: hexane-ethyl acetate (8:2). 0.9 g, Yield: 79%. Solid, mp 115-117° C. $^1$H-NMR (CDCl$_3$, 300 Hz): 7.99 (1H, d, J=8.4 Hz), 7.80 (1H, dd, J=0.9 and 7.8 Hz), 7.72 (1H, m), 7.55 (1H, dd, J=0.9 and 7.5 Hz), 7.33 (2H, s), 6.66 (1H, dd, J=2.1 and 8.4 Hz), 6.58 (1H, d, J=2.1 Hz), 3.97 (6H, s), 3.90 (3H, s), 3.88 (6H, s). $^{13}$C-NMR (CDCl$_3$, 75 Hz): 161.3, 158.4, 156.3, 155.1, 153.4, 138.8, 136.3, 135.7, 132.2, 123.0, 122.1, 117.6, 105.1, 104.2, 98.8, 60.9, 56.2, 55.6, 55.4. MS-EI: 381 (M$^+$). HRMS (ESI(+)): Calcd. for $C_{22}H_{24}NO_5$(M+H): 382.1654. Found: 382.1644.

2-(2,4-Dimethoxyphenyl)-6-(4-methoxyphenyl)pyridine (4h): Eluent: hexane-ethyl acetate (8:2). 0.87 g, Yield: 90%. Solid, mp 97-98° C. $^1$H-NMR (CDCl$_3$, 300 Hz): 8.04 (2H, d, J=8.7 Hz), 8.00 (1H, d, J=8.4 Hz), 7.75 (1H, dd, J=1.2 and 8.1 Hz), 7.69 (1H, m), 7.54 (1H, dd, J=1.5 and 7.5 Hz), 6.99 (1H, d, J=9.0 Hz), 6.65 (1H, dd, J=2.4 and 8.7 Hz), 6.56 (1H, d, J=2.4 Hz), 3.864 (3H, s), 3.861 (3H, s), 3.856 (3H, s). $^{13}$C-NMR (CDCl$_3$, 75 Hz): 161.3, 160.2, 158.4, 156.3, 155.1, 136.3, 132.5, 132.3, 128.2, 122.4, 122.3, 117.1, 116.1, 114.8, 114.0, 105.1, 98.9, 55.6, 55.4, 55.3. MS-EI: 321 (M$^+$). HRMS (ESI(+)): Calcd. for $C_{20}H_{20}NO_3$ (M+H): 322.1443. Found: 322.1434.

5-(3,4-Dimethoxyphenyl)-2-(3,4,5-trimethoxyphenyl)pyridine (4i): Eluent hexane-ethyl acetate (7:3). 1.0 g, Yield: 88%. Solid, mp 131-132° C. $^1$H-NMR (CDCl$_3$, 300 Hz): 8.88 (1H, d, J=2.4 Hz), 7.91 (1H, dd, J=2.4 and 8.1 Hz), 7.75 (1H, d, J=8.4 Hz), 7.29 (2H, s), 7.20 (1H, dd, J=2.4 and 8.1 Hz), 7.13 (1H, d, J=2.1 Hz), 7.00 (1H, d, J=8.4 Hz), 3.99 (6H, s), 3.98 (3H, s), 3.95 (3H, s), 3.92 (3H, s). $^{13}$C-NMR (CDCl$_3$, 75 Hz): 155.2, 153.5, 149.4, 149.2, 147.6, 139.0, 134.7, 134.6, 130.4, 120.0, 119.4, 111.7, 110.0, 103.9, 60.9, 56.2, 56.0. MS-EI: 381 (M$^+$). HRMS (ESI(+)): Calcd. for $C_{22}H_{24}NO_5$ (M+H): 382.1654. Found: 382.1638.

4-(6-(4-Methoxyphenyl)pyridine-2-yl)phenol (4j): Eluent: hexane-ethyl acetate (7:3). 0.60 g, Yield: 73%. Solid, mp 133-134° C. $^1$H-NMR (DMSO-d6, 300 Hz): 9.78 (1H, s), 8.15 (2H, d, J=8.7 Hz), 8.05 (2H, d, J=8.4 Hz), 7.81 (1H, m), 7.74-7.70 (2H, m), 7.05 (2H, d, J=8.7 Hz), 6.90 (2H, d, J=8.4 Hz), 3.82 (3H, s). $^{13}$C-NMR (DMSO-d6, 75 Hz): 160.2, 158.6, 155.6, 155.1, 138.0, 131.4, 129.8, 128.04, 127.95, 116.9, 115.6, 114.1, 55.3. MS-EI: 277 (M$^+$). HRMS (ESI(+)): Calcd. for $C_{18}H_{16}NO_2$ (M+H): 278.1181. Found: 278.1171.

4-(6-(2,4-Dimethoxyphenyl)pyridine-2-yl)phenol (4k): Eluent: hexane-ethyl acetate (7:3). 0.44 g, Yield: 48%. Solid, mp 112-114° C. (d). $^1$H-NMR (DMSO-d6, 300 Hz): 9.74 (1H, s), 7.98 (2H, d, J=8.7 Hz), 7.90 (1H, d, J=9.0 Hz), 7.77-7.66 (3H, m), 6.88 (2H, d, J=8.7 Hz), 6.70-6.68 (2H, m), 3.85 (3H, s), 3.83 (3H, s). $^{13}$C-NMR (DMSO-d6, 75 Hz): 161.1, 158.5, 158.2, 155.6, 154.3, 136.8, 131.7, 130.0, 128.0, 121.9, 121.3, 116.6, 115.5, 105.7, 98.7. MS-EI: 307 (M$^+$). HRMS (ESI(+)): Calcd. for $C_{19}H_{18}NO_3$ (M+H): 308.1285. Found: 308.1276.

2-(2,4-Dimethoxyphenyl)-6-(3,5-dimethoxyphenyl)pyridine (4l): Eluent: hexane-ethyl acetate (9:1). 0.66 g, Yield: 63%. Solid, mp 96-98° C. $^1$H-NMR (CDCl$_3$, 300 Hz): 8.02 (1H, d, J=8.7 Hz), 7.83 (1H, d, J=7.5 Hz), 7.72 (1H, m), 7.57 (1H, d, J=7.8 Hz), 7.26 (2H, s), 6.66 (1H, dd, J=2.1 and 8.4 Hz), 6.57 (1H, d, J=1.8 Hz), 6.53 (1H, m), 3.88 (12H, s). $^{13}$C-NMR (CDCl$_3$, 75 Hz): 161.3, 161.0, 158.4, 156.2, 155.0, 142.1, 136.3, 132.3, 123.3, 122.1, 117.9, 105.1, 100.8, 98.8, 55.6, 55.5. MS-EI: 351 (M$^+$). HRMS (ESI(+)): Calcd. for $C_{21}H_{22}NO_4$ (M+H): 352.1549. Found: 352.1541.

2-(2,4-Dimethoxyphenyl)-6-(2,5-dimethoxyphenyl)pyridine (4m): Eluent: hexane-ethyl acetate (7:3). 0.75 g, Yield: 71%. Solid, mp 76-77° C. $^1$H-NMR (CDCl$_3$, 300 Hz): 7.93 (1H, d, J=8.4 Hz), 7.79-7.66 (3H, m), 7.53 (1H, d, J=2.7 Hz), 6.96-6.87 (2H, m), 6.62 (1H, dd, J=2.4 and 8.7 Hz), 6.56 (1H, d, J=2.1 Hz), 3.86 (3H, s), 3.85 (3H, s), 3.83 (3H, s), 3.80 (3H, s). $^{13}$C-NMR (CDCl$_3$, 75 Hz): 161.2, 158.2, 155.1, 154.9, 153.9, 151.5, 153.3, 132.2, 130.5, 122.8, 122.5, 122.4, 116.5, 114.9, 113.1, 105.0, 98.8, 56.5, 55.8, 55.6, 55.4. MS-EI: 351 (M$^+$). HRMS (ESI(+)): Calcd. for $C_{21}H_{22}NO_4$ (M+H): 352.1549. Found: 352.1560.

2-(2,3-Dimethoxyphenyl)-6-(2,4-dimethoxyphenyl)pyridine (4n): Eluent: hexane-ethyl acetate (9:1). 0.95 g, Yield: 90%. Solid, mp 79-80° C. $^1$H-NMR (CDCl$_3$, 300 Hz): 7.96 (1H, d, J=8.4 Hz), 7.80 (1H, dd, J=2.1 and 7.2 Hz), 7.76-7.68 (2H, m), 7.50 (1H, dd, J=1.5 and 7.8 Hz), 7.16 (1H, t, J=8.1 Hz), 6.96 (1H, dd, J=1.5 and 7.8 Hz), 6.63 (1H, dd, J=2.4 and 8.4 Hz), 6.56 (1H, d, J=2.4 Hz), 3.91 (3H, s), 3.87 (3H, s), 3.85 (3H, s), 3.71 (3H, s). $^{13}$C-NMR (CDCl$_3$, 75 Hz): 161.2, 158.2, 155.1, 155.0, 153.0, 147.2, 153.6, 134.9, 132.2, 124.1, 123.0, 122.9, 122.2, 112.3, 105.1, 98.8, 61.0, 55.9, 55.5, 54.4. MS-EI: 351 (M$^+$). HRMS (ESI(+)): Calcd. for $C_{21}H_{22}NO_4$ (M+H): 352.1549. Found: 352.1557.

2-(2,4-Dimethoxyphenyl)-6-(2,6-dimethoxyphenyl)pyridine (4o): Eluent: hexane-ethyl acetate (8:2). 1.0 g, Yield: 96%. Solid, mp 155-156° C. $^1$H-NMR (CDCl$_3$, 300 Hz):

7.79 (1H, d, J=8.4 Hz), 7.74-7.67 (2H, m), 7.29 (1H, t, J=7.8 Hz), 7.18 (1H, dd, J=2.1 and 6.9 Hz), 6.64 (2H, d, J=8.4 Hz), 6.58 (1H, dd, J=2.4 and 8.4 Hz), 6.54 (1H, d, J=2.1 Hz), 3.85 (3H, s), 3.83 (3H, s), 3.74 (6H, s). $^{13}$C-NMR (CDCl$_3$, 75 Hz): 160.9, 158.3, 158.0, 155.2, 153.8, 135.2, 132.6, 129.4, 123.6, 122.8, 122.7, 119.8, 105.0, 104.4, 98.6, 56.0, 55.5, 55.4. MS-EI: 351 (M$^+$). HRMS (ESI(+)): Calcd. for C$_{21}$H$_{22}$NO$_4$ (M+H): 352.1549. Found: 352.1536.

2-(2,4-Dimethoxyphenyl)-6-(3-methoxyphenyl)pyridine (4p): Eluent: hexane-ethyl acetate (9:1). 0.66 g, Yield: 68%. Solid, mp 75-76° C. $^1$H-NMR (CDCl$_3$, 300 Hz): 8.03 (1H, d, J=8.7 Hz), 7.82 (1H, dd, J=0.6 and 7.8 Hz), 7.75-7.69 (2H, m), 7.65 (1H, d, J=7.8 Hz), 7.59 (1H, dd, J=0.6 and 7.5 Hz), 7.38 (1H, t, J=7.8 Hz), 6.95 (1H, dd, J=1.8 and 8.1 Hz), 6.66 (1H, dd, J=2.4 and 8.7 Hz), 6.56 (1H, d, J=2.1 Hz), 3.89 (3H, s), 3.87 (6H, s). $^{13}$C-NMR (CDCl$_3$, 75 Hz): 161.3, 159.9, 158.4, 156.3, 155.1, 141.4, 136.3, 132.3, 129.5, 123.2, 122.1, 119.4, 117.9, 114.3, 112.4, 105.1, 98.8, 55.6, 55.4, 55.3. MS-EI: 321 (M$^+$). HRMS (ESI(+)): Calcd. for C$_{20}$H$_{20}$NO$_3$ (M+H): 322.1443. Found: 322.1452.

2-(2,4-Dimethoxyphenyl)-6-(2,4,6-trimethoxyphenyl)pyridine (4q): Eluent: hexane-ethyl acetate (7:3). 0.65 g, Yield: 57%. Solid, mp 144-145° C. $^1$H-NMR (CDCl$_3$, 300 Hz): 7.79 (1H, d, J=8.7 Hz), 7.72-7.65 (2H, m), 7.16 (1H, dd, J=2.1 and 6.6 Hz), 6.58 (1H, dd, J=2.1 and 8.4 Hz), 6.53 (1H, d, J=2.1 Hz), 6.22 (2H, s), 3.85 (6H, s), 3.83 (3H, s), 3.73 (6H, s). $^{13}$C-NMR (CDCl$_3$, 75 Hz): 161.1, 160.9, 159.0, 158.0, 155.1, 153.8, 135.1, 132.6, 123.9, 122.8, 122.5, 113.1, 105.0, 98.6, 91.1, 56.0, 55.5, 55.4. MS-EI: 381 (M$^+$). HRMS (ESI(+)): Calcd. for C$_{22}$H$_{24}$NO$_5$ (M+H): 382.1654. Found: 382.1662.

2-(2,4-Dimethoxyphenyl)-6-(2-methoxyphenyl)pyridine (4r): Eluent: hexane-ethyl acetate (9:1). 0.86 g, Yield: 89%. Solid, mp 95-96° C. $^1$H-NMR (CDCl$_3$, 300 Hz): 7.94 (1H, d, J=8.7 Hz), 7.92 (1H, dd, J=1.8 and 7.8 Hz), 7.77-7.65 (3H, m), 7.36 (1H, m), 7.08 (1H, td, J=1.2 and 7.5 Hz), 7.00 (1H, d, J=8.1 Hz), 6.62 (1H, dd, J=2.4 and 8.7 Hz), 6.56 (1H, d, J=2.4 Hz), 3.87 (3H, s), 3.86 (3H, s), 3.85 (3H, s). $^{13}$C-NMR (CDCl$_3$, 75 Hz): 161.1, 158.2, 157.1, 155.2, 155.1, 135.2, 132.3, 131.5, 129.7, 129.6, 122.7, 122.6, 122.5, 121.0, 111.4, 105.1, 98.8, 55.64, 55.61, 55.4. MS-EI: 321 (M$^+$). HRMS (ESI(+)): Calcd. for C$_{20}$H$_{20}$NO$_3$ (M+H): 322.1443. Found: 322.1435.

5-(6-(2,4-Dimethoxyphenyl)pyridine-2-yl)-2-methoxyphenol (4s): Eluent: hexane-ethyl acetate (7:3). 0.84 g, Yield: 83%. Solid, mp 142-144° C. $^1$H-NMR (DMSO-d6, 300 Hz): 9.16 (1H, s), 7.89 (1H, d, J=9.3 Hz), 7.78-7.66 (4H, m), 7.53 (1H, dd, J=1.8 and 8.4 Hz), 7.01 (1H, d, J=8.4 Hz), 6.70-6.69 (2H, m), 3.86 (3H, s), 3.83 (3H, s), 3.82 (3H, s). $^{13}$C-NMR (DMSO-d6, 75 Hz): 161.1, 158.2, 155.4, 154.3, 148.7, 146.7, 136.8, 132.0, 131.7, 122.2, 121.2, 117.7, 116.9, 113.7, 112.1, 105.7, 98.7, 55.72, 55.66, 55.4. MS-EI: 337 (M$^+$). HRMS (ESI(+)): Calcd. for C$_{20}$H$_{20}$NO$_4$(M+H): 338.1392. Found: 338.1386.

2-Methoxy-5-(6-(3,4,5-trimethoxyphenyl)pyridine-2-yl)phenol (4t): Eluent: hexane-ethyl acetate (7:3). 0.72 g, Yield: 66%. Solid, mp 129-130° C. $^1$H-NMR (DMSO-d6, 300 Hz): 9.24 (1H, s), 7.87 (2H, d, J=4.2 Hz), 7.76 (1H, m), 7.71 (1H, d, J=2.1 Hz), 7.60 (1H, dd, J=2.1 and 8.4 Hz), 7.48 (2H, s), 7.03 (1H, d, J=8.4 Hz), 3.91 (6H, s), 3.83 (3H, s), 3.73 (3H, s). $^{13}$C-NMR (DMSO-d6, 75 Hz): 155.4, 155.1, 153.2, 148.9, 146.7, 138.6, 138.0, 134.5, 131.5, 118.1, 117.9, 113.7, 112.2, 104.1, 60.2, 56.1, 55.7. MS-EI: 367 (M$^+$). HRMS (ESI(+)): Calcd. for C$_{21}$H$_{22}$NO$_5$ (M+H): 368.1498. Found: 368.1490.

2-(2,4-Dimethoxyphenyl)-6-(3-hydroxy-4-methoxyphenyl) pyridin-1-ium chloride (5): To the solution of 4s (0.3 g, 0.88 mmol) in THF (5 mL) was added HCl solution in ether (0.44 mL, 0.88 mmol, 2 M). The resultant mixture was stirred at rt overnight. The precipitate was filtered and washed with dichloromethane to afford 5 (0.32 g) in yield of 97%. Solid, mp 140° C. (d). $^1$H-NMR (DMSO-d6, 300 Hz): 8.28 (1H, t, J=7.8 Hz), 7.96 (1H, d, J=7.8 Hz), 7.89 (1H, d, J=7.8 Hz), 7.75 (1H, d, J=8.4 Hz), 7.45-7.42 (2H, m), 7.13 (1H, d, J=8.7 Hz), 3.92 (3H, s), 3.861 (3H, s), 3.855 (3H, s). $^{13}$C-NMR (DMSO-d6, 75 Hz): 163.1, 158.6, 152.8, 151.6, 150.6, 147.1, 143.1, 132.5, 126.4, 124.1, 121.0, 119.9, 115.7, 114.8, 112.5, 106.4, 99.0, 56.3, 56.0, 55.9. MS-ESI: 338 (M$^+$-Cl). HRMS (ESI(+)): Calcd. for C$_{20}$H$_{20}$NO$_4$(M-Cl): 338.1392. Found: 338.1387.

Table 1 shows that pyridine-bridged CA-4 analogs potently inhibit MDA-MB-231, A459 and HeLa cancer cell survival and growth.

TABLE 1

Growth inhibition IC$_{50}$ values of synthetic pyridine-bridged CA-4 analogs in three metastatic cancer cell lines: MDA-MB-231, A549, and HeLa

| Combretastatin analogs | Growth Inhibition IC$_{50}$ (μM) | | |
|---|---|---|---|
| | MDA-MB-231 | A549 | HeLa |
| 2a | 6 | 9 | 12 |
| 2b | >25 | >25 | >50 |
| 2c | >100 | >50 | >50 |
| 2d | 10 | 2 | 2 |
| 2e | 12 | >25 | 14 |
| 2f | >100 | >100 | >25 |
| 3a | 11 | >50 | 1 |
| 3b | >50 | >50 | >25 |
| 3c | 0.075 | 0.079 | 0.011 |
| 3d | 9 | >100 | 2 |
| 3e | 11 | >100 | 2.68 |
| 3f | 2.63 | 7.86 | 0.79 |
| 3g | >100 | >100 | >50 |
| 3h | >50 | >50 | >25 |
| 4a | 10 | >25 | 8 |
| 4b | >50 | >100 | 0.86 |
| 4c | 2.49 | >50 | 0.026 |
| 4d | >25 | >25 | >25 |
| 4e | 13 | >25 | >50 |
| 4f | >25 | >50 | >50 |
| 4g | >100 | 0.69 | 4.43 |
| 4h | 0.0031 | 0.089 | 0.0038 |
| 4i | >50 | >50 | >25 |
| 4j | >25 | >25 | >50 |
| 4k | 17.2 | 4.22 | >100 |
| 4l | >25 | >25 | >50 |
| 4m | 0.034 | 0.33 | 0.034 |
| 4n | >50 | >51 | >52 |
| 4o | >100 | >100 | >50 |
| 4p | 9.02 | 0.56 | 0.067 |
| 4q | >50 | >50 | >25 |
| 4r | >25 | >50 | >25 |
| 4s | 0.0046 | 0.044 | 0.0014 |
| 4t | 0.069 | 2.64 | 0.0047 |
| 5 | 0.0054 | 0.042 | 0.0026 |
| CA-4 | 0.0028 | 0.0038 | 0.0009 |

EXAMPLE 2

Antiproliferative Assays of Pyridine-bridged CA-4 Analogs

Human breast adenocarcinoma (MDA-MB-231), human nonsmall cell lung carcinoma (A549), and human cervix carcinoma (HeLa) cells were grown in DMEM medium supplemented with 115 units/mL of penicillin G, 115 μg/mL of streptomycin, and 10% fetal bovine serum (all from Life Technologies, Grand Island, N.Y.). Cells were seeded in 96-well plates ($5 \times 10^3$ cells/well) containing 50 µL growth medium for 24 hours. After medium removal, 100 µL fresh medium containing individual analog compound at different concentrations was added to each well and incubated at 37° C. for 72 h. After 24 h of culture, the cells were supplemented with 50 µL of analog compounds dissolved in DMSO (less than 0.25% in each preparation). After 72 h of incubation, 20 µL of resazurin was added for 2 h before recording fluorescence at 560 nm (excitation) and 590 nm (emission) using a Victor microtiter plate fluorimeter (Perkin-Elmer, USA). The $IC_{50}$ was defined as the compound concentration required to inhibit cell proliferation by 50%, in comparison with cells treated with the maximum amount of DMSO (0.25%) and considered as 100% viability.

EXAMPLE 3

Immunofluorescence

MDA-MB-231 and HeLa cells were grown on a Laboratory-Tek chamber slide (VWR International, Radnor, Pa.) and treated with vehicle (DMSO) or 1 µM CA-4 or 4h for 24 hours to 4 days. At the completion of treatment, cells were fixed with 3.7% formaldehyde and permeabilized with 0.1% Triton X-100 in PBS for 4 min. The cells were first incubated for 1 h in a solution of PBS containing 1% BSA and calf serum to block nonspecific antibody binding. The cells were then incubated with the mouse anti-tubulin antibody (1:200) (Life Technologies, Grand Island, N.Y.), washed 3 times in PBS containing 1% BSA and incubated for 2 h at room temperature with secondary goat antimouse antibody Alexa 488 labeled (1:200) for tubulin staining. The chamber slides were examined and photographed using a Nikon ES800 fluorescence microscope with a digital camera.
Antimicrotubule Effects in HeLa and MDA-MB-231Cells To determine the microtubule disrupting effects of the pyridine-linked analogs, compound 4h was selected as a representative compound in a cell-based phenotypic screening. HeLa and MDA-MB-231 cells were used to examine the effect of 4h on the reorganization of microtubules during mitosis. Cells were treated with either 4h or CA-4 for 24 h, and microtubules were visualized by indirect immunofluorescence techniques. An antibody for β-tubulin was used to visualize interphase and mitotic microtubule structures. Vehicle-treated cells exhibited a normal filamentous microtubule array, with microtubules extending from the central regions of the cell to the cell periphery (FIG. 37A, D). Compound 4h caused dramatic reduction of the interphase microtubule network, as shown in FIG. 37C in HeLa cells and in FIG. 37F for MDA-MB-231 cells. As demonstrated in FIGS. 37B and 37E for the two cell lines respectively, CA-4 induced very similar loss of the microtubule network.

Figure 37:
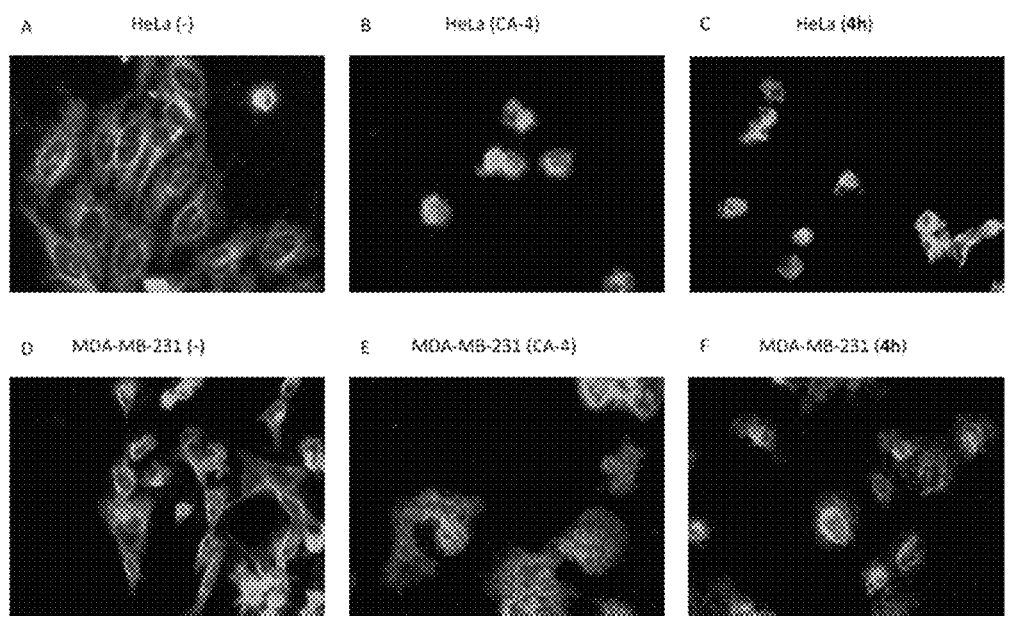
FIG. 37 shows the effects of CA-4 and 4h on interphase microtubules.

At FIG. 37 the effects of CA-4 and 4h on interphase microtubules are shown. MDA-MB-231 and HeLa cells were treated with vehicle (A, D) or 1 µM compounds (B, C and E, F) as indicated for 24 hours. Cells were then fixed and microtubules visualized by indirect immunofluorescence techniques. Normal interphase microtubules are visible in the control cells of HeLa and MDA-MB-231. The loss of interphase microtubules induced by CA-4 and 4h is shown in respective treatments as labeled.

EXAMPLE 4

Tubulin Polymerization Assays

Figure 39:
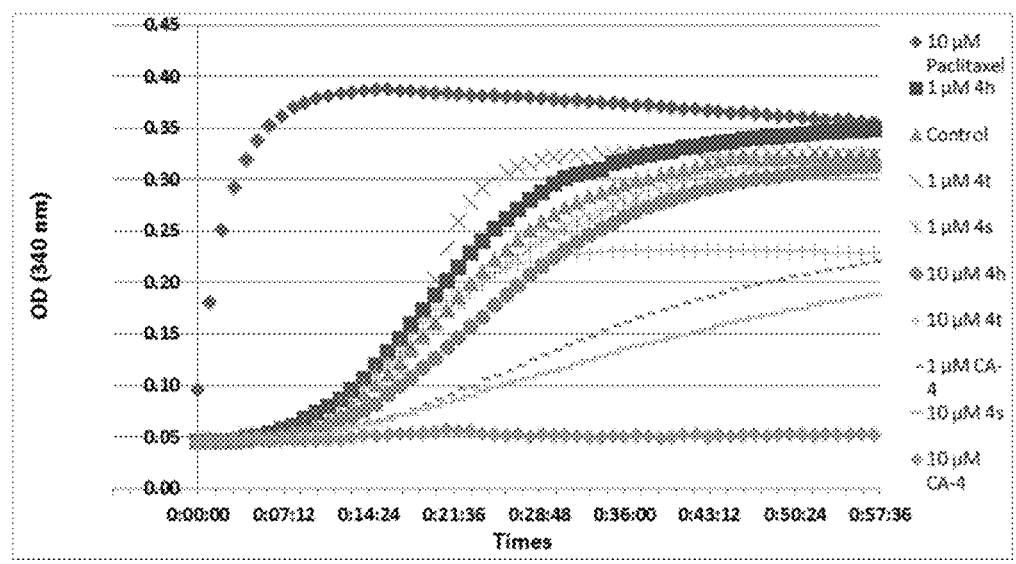
FIG. 39 shows effects of pyridine-linked CA-4 analogs on microtubule dynamics.

A tubulin polymerization kit (Cytoskeleton, Denver, Colo.) was used to evaluate effect of the pyridine-linked CA-4 analogs on tubulin assembly in vitro[24-25]. It is based on the principal that light is scattered by microtubules to an extent that is proportional to the concentration of the microtubule polymer. Compounds that interact with tubulin will alter the polymerization of tubulin, and this can be detected using a spectrophotometer. The absorbance at 340 nm at 37° C. is monitored. The experimental procedure of the assay was performed as described in version 8.2 of the tubulin polymerization assay kit manual. Varying concentrations of compounds were preincubated with 10 µM bovine brain tubulin in glutamate buffer at 30° C. and then cooled to 0° C. After the addition of 0.4 mM GTP, the mixtures were transferred to 0° C. cuvettes in a recording spectrophotometer and warmed to 30° C. Tubulin assembly was followed turbidimetrically at 350 nm.
Inhibition of Tubulin Polymerization In Vitro The inhibition of tubulin polymerization by the pyridine-linked CA-4 analog 4h, 4s, and 4t were tested using bovine brain tubulin. As shown in FIG. 39, incubation with either vehicle (DMSO), CA-4, 4h, 4s, or 4t resulted in various degrees of inhibition of tubulin polymerization, depending on the compound and the dose. At 1 µM, all pyridine-linked analogs (4h, 4s, and 4t) failed to inhibit tubulin polymerization. Compared to vehicle, 4h at this concentration appeared to be slightly stimulating tubulin polymerization. In contrast, CA-4 at 1 µM inhibited tubulin polymerization by 35%. When analog concentrations were increased to 10 µM, 4h remained ineffective against tubulin polymerization, whereas 4s and 4t were seen to inhibit tubulin polymerization by 57% and 32%, respectively. In comparison, CA-4 at 10 µM nearly completely blocked tubulin polymerization (FIG. 39). These data suggest that it is possible for the pyridine-linked analogs to have potent cytotoxicity but very little anti-tubulin polymerization activity, such as 4h.

At FIG. 39, effects of pyridine-linked CA-4 analogs on microtubule dynamics are shown. Polymerization of tubulin at 37° C. in the presence of paclitaxel (10 µM), CA-4 (1 µM and 10 µM), 4h (1 µM and 10 µM), 4s (1 and 10 µM), and 4t (1 and 10 µM), and were monitored continuously by measuring the absorbance at 340 nm over 60 min. The reaction was initiated by the addition of tubulin to a final concentration of 3.0 mg/mL

EXAMPLE 5

Cytofluorimetric Analysis of Cell Cycle Distribution

Figure 38:
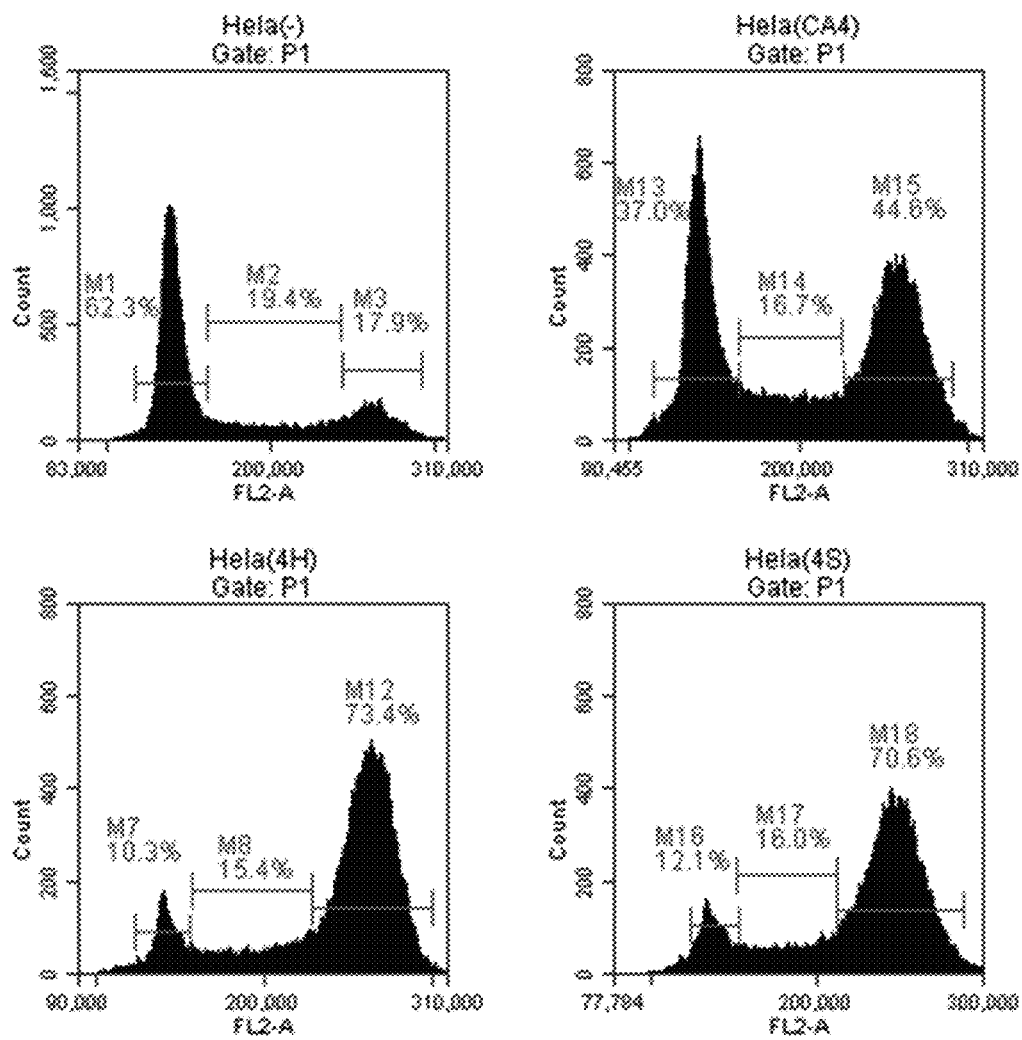
FIG. 38 shows cytometric analysis of cell cycle distributions of HeLa cells treated with pyridine analogs 4h and 4s.

Cells treated with tested compounds for 24 h were washed once in PBS and resuspended in 1 mL of 70% ice cold ethanol and stored at −20° C. Fixed cells were washed twice in PBS and then treated with 1 mL of 0.1 mg/mL of RNase. A solution at 37° C. for 1 h. DNA was then stained with a PBS solution containing 0.1 mg/mL propidium iodide for 30 min at room temperature in the dark. Cell cycle analysis was determined with Accuri C6 (BD Biosciences, Mountain View, Calif.).
Effect on Cell Cycle Arrest To investigate the effect of the pyridine-linked CA-4 analogs on cell cycle arrest, flow cytometry was used to analyze the cell cycle distribution of HeLa cells following treatment with 4h and 4s at 1 µM. Untreated cells were used as a negative control, and cells treated with CA-4 were used as a positive control. As shown in FIG. 38, the two most potent CA-4 analogs, 4h and 4s were found to be as effective in arresting the cell cycle at G2/M phase as CA-4. With the untreated cells, the percentage of cells in the G0/G1 phase was at 61.60% with only 15.70% in the G2/M phase. After treatment with 4h or 4s, the percentage of cells in the G2/M phase increased to 73.40% and 70.60%, respectively. These results compare favorably to 44.60% in the G2/M phase for cells treated with CA-4.

Similar results were obtained when another metastatic cancer cell line, MDA-MB-231 was used to test the effect of these compounds on cell cycle arrest. At 1 µM concentration, 4h and 4s again showed strong cell cycle inhibition. As indicated in Table 2, after treatment with 4h and 4s, 73.4% and 70.6% of HeLa cells were arrested in the G2/M phase, respectively, whereas treatment with CA-4 resulted in 44.6% G2/M phase cells. Similarly, the percentage of MDA-MB-231 cells in the G2/M phase increased from 15.50% (control) to 57.80% (CA-4 treated), 70.5 (4h treated), and 54.1 (4s treated).

TABLE 2

Cell cycle distribution for HeLa and MDA-MB-231 cells after treatment with CA-4, 4h, and 4s.

|  | G0/G1 | S | G2/M |
| --- | --- | --- | --- |
| HeLa cells |  |  |  |
| Control (—) | 61.60% | 22.10% | 15.70% |
| Treated with CA-4 | 37.00% | 16.70% | 44.60% |
| Treated with 4h | 10.30% | 15.40% | 73.40% |
| Treated with 4s | 12.10% | 17.10% | 70.60% |
| MDA-MB-231 cells |  |  |  |
| Control (—) | 58.60% | 25.70% | 15.50% |
| Treated with CA-4 | 27.50% | 11.80% | 57.80% |
| Treated with 4h | 13.10% | 16.40% | 70.50% |
| Treated with 4s | 18.60% | 17.10% | 54.10% |

EXAMPLE 6

Chick Embryo Chorioallantoic Membrane (CAM) Assay

Fertilized embryos were obtained from Charles River Laboratories and incubated at 37.5° C. for 3 days, removed from their shell using a Dremel tool and placed into a covered weighing boat for 10 further days of incubation. Solidified 30 □L onplants containing 2.1 mg/mL rat tail collagen (BD Biosciences, Bedford, Mass.) and 10 ng/mL bFGF and 30 ng/mL VEGF in the presence or absence of CA-4 and 4s were placed on the embryo chorioallantoic membrane (CAM) over two pieces of nylon mesh approximately 0.5 cm². Four collagen onplants were added per egg on at least 3 separate eggs. After four days of incubation, images were taken of each plug on surviving embryos using a mini-Vid camera (LW Scientific; Lawrenceville, Ga.) and quantified in a masked fashion on a scale from 0-3 with 0 representing no angiogenesis and 3 representing extreme angiogenesis. Data from one scorer (confirmed by a second scorer) are presented as the means±standard errors of the mean. Statistical significances were determined by one-way analysis of variance (ANOVA) followed by Dunnett's multiple comparison test (GraphPad Prism, La Jolla, Calif.).

Anti-angiogenesis Assay Using Chick Embryo Chorioallantoic Membrane (CAM)

Figure 40:
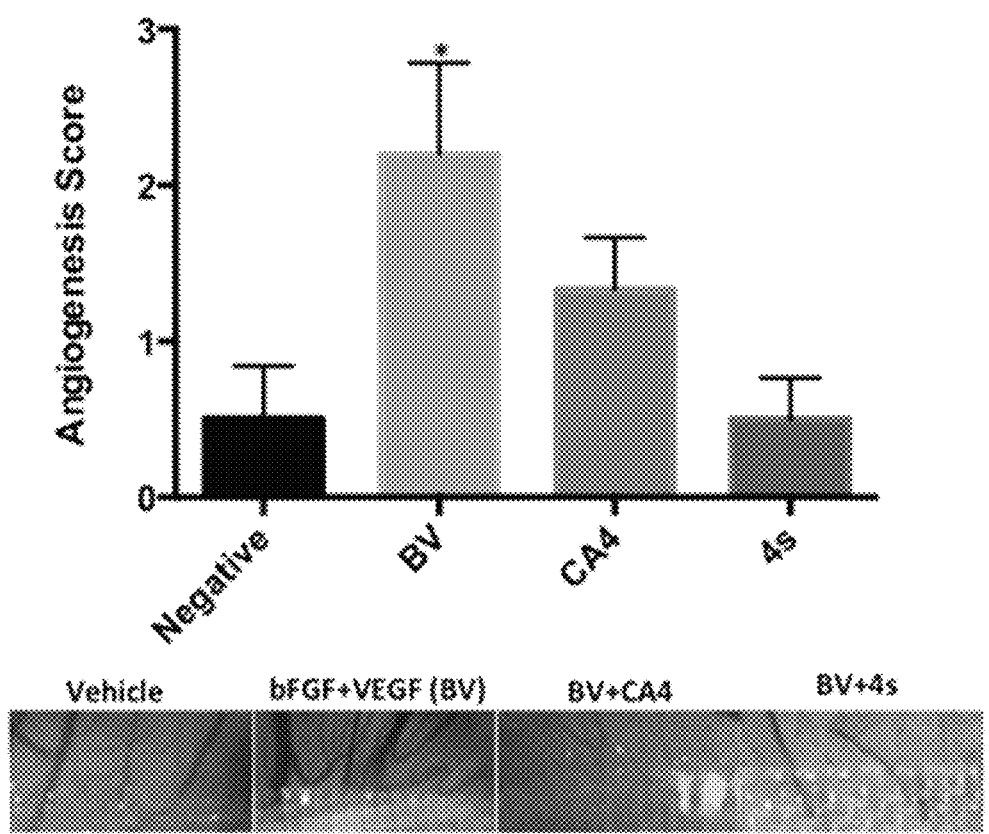
FIG. 40 shows effects of 4s and CA-4 on angiogenesis in chick embryo.

The most potent pyridine-linked combretastatin analog, 4s was then tested for antiangiogenic and vasculature disrupting properties using the CAM assay. In this test the vascular system of a fertilized chicken embryo is used as a model. FIG. 40 demonstrates the effects of 4s and CA-4 on the development of embryonal blood vessels compared to a negative control (PBS) and a positive control (10 ng/plug basic Fibroblast Growth Factor (bFGF) and 25 ng/plug Vascular Endothelial Growth Factor (VEGF)). The anti-angiogenesis activity of 4s and CA-4 were determined by the suppression of angiogenic action of BV (bFGF+VEGF) when the compound was added to a collagen containing BV and placed on the chorioallantoic membrane of 123-day old chick embryos for four days. Angiogenesis was scored by two scorers in a blinded fashion. Both 4s and CA-4 led to inhibition of new vessel growth and vessel shrinkage 4 days after treatment scored on a scale of 0-3 in a blinded manner. The negative control (vehicle), CA-4, and 4s scored significantly lower than the positive control (BV). The CAM assay results suggest that 4s is a potent inhibitor of angiogenesis and is more effective than CA-4 in suppressing new vessel growth.

Methods of Administration

The compounds of the disclosure are useful in vitro or in vivo in inhibiting the growth of cancer cells. The compounds may be used alone or in compositions together with a pharmaceutically acceptable carrier or excipient. Suitable pharmaceutically acceptable carriers or excipients include, for example, processing agents and drug delivery modifiers and enhancers, such as, for example: calcium phosphate, magne-sium stearate, talc, monosaccharides, disaccharides, starch, gelatin, cellulose, methyl cellulose, sodium carboxymethyl cellulose, dextrose, hydroxypropyl-1-cyclodextrin, polyvinyl-pyrrolidinone, low melting waxes, ion exchange resins, and the like, as well as combinations of any two or more thereof. Other suitable pharmaceutically acceptable excipients are described in "Remington's Pharmaceutical Sciences," Mack Pub. Co., New Jersey, 1991, incorporated herein by reference.

Effective amounts of the compounds of the disclosure generally include any amount sufficient to: (1) detectably limit tubulin polymerization in a cell of interest; (2) detectably inhibit cancer proliferation or (3) alleviate symptoms of cancer in a patient or animal treated with a pyridine-bridged analog of CA-4 described herein.

The amount of pyridine-bridged analog of CA-4 active ingredient that may be combined with the carrier materials to produce a single dosage form will vary depending upon the host treated and the particular mode of administration. It will be understood, however, that the specific dose level for any particular patient will depend upon a variety of factors including the activity of the specific pyridine-bridged analog of CA-4 employed, the age, body weight, general health, sex, diet, time of administration, route of administration, rate of excretion, drug combination, and the severity of the particular disease being treated.

Accordingly, the pyridine-bridged analog of CA-4 of the present disclosure can be provided in vivo to a mammal in need thereof, in any manner, for treatment of metastatic cancer for example, with the desired outcome of blocking or delaying the onset of metastasis. The pyridine-bridged analog of CA-4 of the present disclosure can be provided by any route acceptable for administration, and at any dose acceptable for a non-cytotoxic therapeutic agent.

For example, the pyridine-bridged analogs of CA-4 of the present disclosure can be provided at 1 mg, 5 mg, 10 mg, 20 mg, 30 mg, and 40 mg per day per kilogram per animal. A particular embodiment of the present disclosure, entails an application of the pyridine-bridged analog of CA-4 compound 4s and 4h at the aforementioned dosages.

As aforementioned, the pyridine-bridged analog of CA-4 of the present disclosure can be administered at about 1 mg to about 40 mg/kg of body weight daily, in a human or animal, being so treated. Further, a therapeutically effective dosage of a pyridine-bridged analog of CA-4 compound or composition comprising such a compound, may include a total daily dose administration of for example, from about 0.001 to 1000 mg/kg of body weight daily, or from about 0.01 to 100 mg/kg of body weight daily, or from about 0.1 to 10 mg/kg of body weight daily. Dosage unit compositions may contain such amounts of submultiples thereof to make up the daily dosages.

The pyridine-bridged analogs of the present disclosure may be administered orally, parenterally, sublingually, by aerosolization or inhalation of a spray, rectally, or topically, in dosage unit formulations containing conventional non-toxic pharmaceutically acceptable carriers, adjuvants, and vehicles as desired. Topical administration may also involve the use of transdermal administration such as transdermal patches.

Injectable preparations, for example, sterile injectable aqueous or oleaginous suspensions may be formulated according to the known art using skiable dispersing or wetting agents and suspending agents.

Solid dosage forms for oral administration may include capsules, tablets, pills, powders, and granules. In such solid dosage forms, the active pyridine-bridged analog may be admixed with at least one inert diluent such as sucrose, lactose, or starch. Such dosage forms may also comprise, as is normal practice, additional substances other than inert diluents.

While various preferred embodiments of the invention have been disclosed above, it will be appreciated that changes can be made to these embodiments without departing from the spirit and scope of the invention.

REFERENCES

1. Jordan, A.; Hadfield, J. A.; Lawrence, N. J.; Mcgown, A. T. Tubulin as a target for anticancer drugs: Agents which interact with the mitotic spindle. *Med. Res. Rev.* 1998, 18, 259-296.
2. Giannakakou, P.; Sackett, D.; Fojo, T. Tubulin/microtubules: still a promising target for new chemotherapeutic agents. *J. Natl. Cancer Inst.* 2000, 92, 182-183.
3. Checchi, P. M.; Nettles, J. H.; Zhou, J.; Snyder, J. P.; Joshi, H. C. Microtubule-interacting drugs for cancer treatment. *Trends Pharmacol. Sci.* 2003, 24, 361-365.
4. Pettit, G. R.; Cragg, G. M.; Herald, D. L.; Schmidt, J. M.; Lohavanijaya, P. Isolation and structure of combretastatin. *Can. J. Chem.* 1982, 60, 1374-1376.
5. Pettit, G. R.; Temple, J. R. C.; Narayanan, V.; Varma, R.; Simpson, M. J.; Boyd, M. R.; Rener, G. A.; Bansal, N. Antineoplastic agents 322. synthesis of combretastatin A-4 prodrugs. *Anti-cancer Drug Des.* 1995, 10, 299-309.
6. Patterson, D.; Rustin, G. Vascular damaging agents. *Clin. Oncol.* 2007, 19, 443-456.
7. Dowlati, A.; Robertson, K.; Cooney, M.; Petros, W. P.; Stratford, M.; Jesberger, J.; Rafie, N.; Overmoyer, B.; Makkar, V.; Stambler, B.; Taylor, A.; Waas, J.; Lewin, J. S.; McCrae, K. R.; Remick, S. C. A phase I pharmacokinetic and translational study of the novel vascular targeting agent combretastatin a-4 phosphate on a single-dose intravenous schedule in patients with advanced cancer. *Cancer Res.* 2002, 62, 3408-3416.
8. Rustin, G. J; Galbraith, S. M.; Anderson, H.; Stratford. M.; Folkes, L. K.; Sena, L.; Gumbrell, L.; Price, P. M. Phase I clinical trial of weekly combretastatin A4 phosphate: clinical and pharmacokinetic results. *J. Clin. Oncol.* 2003, 21. 2815-2822.
9. Stevenson J p, Rosen M, Sun W et al.: Phase I trial of the antivascular agent combretastatin A4 phosphate on a 5-day schedule to patients with cancer: magnetic resonance imaging evidence for altered tumor blood flow. *J. Clin. Oncol.* 2003, 21, 4428-4438.
10. Mooney Cj, Nagaiah G, Fu P et al.: A phase II trial of fosbretabulin in advanced anaplastic thyroid carcinoma and correlation of baseline serum-soluble intracellular adhesion molecule-1 with outcome. *Thyroid* 2009, 19, 233-240.
11. Tron, G. C.; Pirali, T.; Sorba, G.; Pagliai, F.; Busacca, S.; Genazzani, A. A. Medicinal chemistry of combretastatin A4: present and future directions. *J. Med. Chem.* 2006, 49, 3033-3044.
12. Kong, Y.; Grembecka, J.; Edler, M. C.; c et al.: Structure-based discovery of a boronic acid bioisostere of combretastatin A-4. *Chem. Biol.* 2005, 12, 1007-1014.
13. Maya, A. B. S.; Rey, B. D.; Pelaez Lamamie De Clairac, R.; Caballero, E.; Barasoain, I.; Andreu, J. M.; Medarde, M. Design, synthesis and cytotoxic activities of naphthyl analogues of combretastatin A-4. *Bioorg. Med. Chem. Lett.* 2000, 10, 2549-2551.
14. Pettit, G. R.; Minardi, M. D.; Rosenberg, H. J.; Hamel, E.; Bibby, M. C.; Martin, S. W.; Jung, M. K.; Pettit, R. K.; Cuthbertson, T. J.; Chapuis, J. C. Antineoplastic agents. 509. Synthesis of fluorcombstatin phosphate and related 3-halostilbenesll, 1. *J. Nat. Prod.* 2005, 68, 1450-1458.
15. Gaukroger, K.; Hadfield, J. A.; Lawrence, N. J.; Nolan, S.; Mcgown, A. T.
Structural requirements for the interaction of combretastatins with tubulin: how important is the trimethoxy unit? *Org. Biomol. Chem.* 2003, 1, 3033-3037.
16. Ohsumi K, Hatanaka T, Fujita K Nakagawa, R.; Fukuda, Y.; Nihei, Y.; Suga, Y.; Morinaga, Y.; Akiyama, Y.; Tsuji, T. Syntheses and antitumor activity of cis-restricted combretastatins: 5-membered heterocyclic analogues. *Bioorg. Med. Chem. Lett.* 1998, 8, 3153-3158.
17. Bailly, C.; Bal, C.; Barbier, P.; Combes, S.; Finet, J. P.; Hildebrand, M. P.; Peyrot, V. Synthesis and biological evaluation of 4-arylcoumarin analogues of combretastatins. *J. Med. Chem.* 2003, 46, 5437-5444.
18. Pati, H. N.; Wicks, M.; Holt Jr., H. L.; LeBlanc R.; Weisbruch, P.; Forrest, L.; Lee M. Synthesis and biological evaluation of cis-combretastatin analogs and their novel 1, 2, 3-triazole derivatives. *Heterocycl. Commun.* 2005, 11, 117-120.
19. Pettit, G. R.; Toki, B.; Herald, D. L.; Verdier-Pinard, P.; Boyd, M. R.; Hamel, E.; Pettit, R. K. Antineoplastic agents. 379. Synthesis of phenstatin phosphatela. *J. Med. Chem.* 1998, 41, 1688-1695.
20. Ducki, S.; Forrest, R.; Hadfield, J. A.; Kendall, A.; Lawrence, N. J.; McGown, A. T.; Rennison, D. Potent antimitotic and cell growth inhibitory properties of substituted chalcones. *Bioorg. Med. Chem. Lett.* 1998, 8, 1051-1056.
21. Simoni, D.; Grisolia, G.; Giannini, G.; Roberti, M.; Rondanin, R.; Piccagli, L.; Baruchello, R.; Rossi, M.; Romagnoli, R.; Invidiata, F. P.; Grimaudo, S.; Jung, M. K.; Hamel, E.; Gebbia, N.; Crosta, L.; Abbadessa, V.; Di Cristina, A.; Dusonchet, L.; Meli, M.; Tolomeo, M. Heterocyclic and phenyl double-bond-locked combretastatin analogues possessing potent apoptosis-inducing activity in HL60 and in MDR cell lines. *J. Med. Chem.* 2005, 48, 723-736.

What is claimed is:

1. A method of inhibiting tubulin polymerization in a mammal in need thereof, the method comprising administering to the mammal a pharmaceutical composition comprising a compound of the formula:

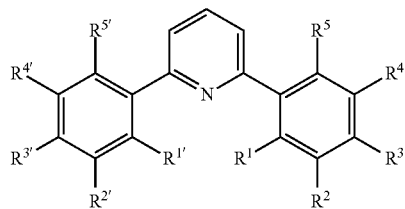

wherein:
$R^1$, $R^2$, $R^3$, $R^4$, and $R^5$ are, independently, H, hydroxyl, methoxy, or ethoxy, in any combinations thereof; and wherein
$R^{1'}$, $R^{2'}$, $R^{3'}$, $R^{4'}$ and $R^{5'}$ are, independently, H, hydroxyl, methoxy, or ethoxy, in any combinations thereof,
or a pharmaceutically acceptable salt thereof,
in an amount effective to inhibit tubulin polymerization in the mammal.

2. The method of claim 1, wherein the compound is selected from the group consisting of: 2,6-bis(3,4,5-trimethoxyphenyl)pyridine; 2,6-bis(3,4-dimethoxyphenyl)pyridine; 2,6-bis(2,4-dimethoxyphenyl)pyridine; and 2,6-bis(4-methoxyphenyl)pyridine.

3. The method of claim 1, wherein the compound is selected from the group consisting of: 4-(6-(3,4,5-trimethoxyphenyl)pyridin-2-yl)phenol; 4-(6-(3,4-dimethoxyphenyl)pyridin-2-yl)phenol; 2-(3,4-bimethoxyphenyl)-6-(3,4,5-trimethoxyphenyl)pyridine; 2-(3,4-dimethoxyphenyl)-6-(4-methoxyphenyl)pyridine; 2-(2,4-dimethoxyphenyl)-6-(3,4-dimethoxyphenyl)pyridine; 2-(4-methoxyphenyl)-6-(3,4,5-trimethoxyphenyl)pyridine; 2-(2,4-dimethoxyphenyl)-6-(3,4,5-trimethoxyphenyl)pyridine; 2-(2,4-dimethoxyphenyl)-6-(4-methoxyphenyl)pyridine; 4-(6-(4-methoxyphenyl)pyridine-2-yl)phenol; 4-(6-(2,4-dimethoxyphenyl)pyridine-2-yl)phenol; 2-(2,4-dimethoxyphenyl)-6-(3,5-dimethoxyphenyl)pyridine; 2-(2,4-dimethoxyphenyl)-6-(2,5-dimethoxyphenyl)pyridine; 2-(2,3-dimethoxyphenyl)-6-(2,4-dimethoxyphenyl)pyridine; 2-(2,4-dimethoxyphenyl)-6-(2,6-dimethoxyphenyl)pyridine; 2-(2,4-dimethoxyphenyl)-6-(3-methoxyphenyl)pyridine; 2-(2,4-dimethoxyphenyl)-6-(2,4,6-trimethoxyphenyl)pyridine; 2-(2,4-dimethoxyphenyl)-6-(2-methoxyphenyl)pyridine; 5-(6-(2,4-dimethoxyphenyl)pyridine-2-yl)-2-methoxyphenol; and 2-methoxy-5-(6-(3,4,5-trimethoxyphenyl)pyridine-2-yl)phenol.

4. The method of claim 1, wherein the compound is 2-(2,4-dimethoxyphenyl)-6-(3-hydroxy-4-methoxyphenyl)pyridin-1-ium chloride.

5. The method of claim 1, wherein said pharmaceutical composition is in the form of a product for oral delivery, selected from the group consisting of a concentrate, dried powder, liquid, capsule, pellet, and pill.

6. The method of claim 1, wherein said pharmaceutical composition is in the form of a product for parenteral administration selected from the group consisting of intravenous, intradermal, intramuscular, and subcutaneous administration.

7. The method of claim 1, wherein said pharmaceutical composition further comprises a carrier, a binder, a diluent, and/or an excipient.

8. The method of claim 1, wherein said pharmaceutical composition further comprises a cancer chemotherapeutic agent.

9. A method of treating a metastatic cancer in a mammal in need thereof, comprising administering a compound of the formula:

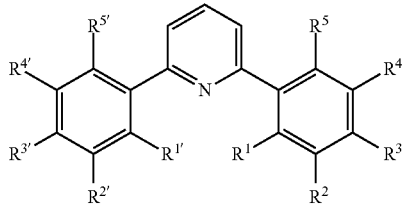

wherein:
$R^1$, $R^2$, $R^3$, $R^4$, and $R^5$ are, independently, H, hydroxyl, methoxy, or ethoxy, in any combinations thereof; and wherein
$R^{1'}$, $R^{2'}$, $R^{3'}$, $R^{4'}$ and $R^{5'}$ are, independently, H, hydroxyl, methoxy, or ethoxy, in any combinations thereof,
or a pharmaceutically acceptable salt thereof,
in an amount effective to treat said metastatic cancer in said mammal.

10. A method of inducing cell cycle arrest in a mammal in need thereof, the method comprising administering to the mammal a pharmaceutical composition comprising a compound of the formula:

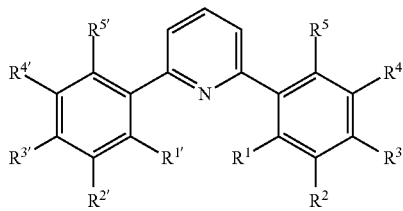

wherein:
$R^1$, $R^2$, $R^3$, $R^4$, and $R^5$ are, independently, H, hydroxyl, methoxy, or ethoxy, in any combinations thereof; and wherein
$R^{1'}$, $R^{2'}$, $R^{3'}$, $R^{4'}$ and $R^{5'}$ are, independently, H, hydroxyl, methoxy, or ethoxy, in any combinations thereof,
or a pharmaceutically acceptable salt thereof,
in an amount effective to induce cell cycle arrest in the mammal.

11. A method of suppressing angiogenesis in a mammal in need thereof, the method comprising administering to the mammal a pharmaceutical composition comprising a compound of the formula:

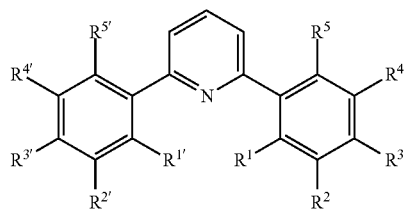

wherein:
R$^1$, R$^2$, R$^3$, R$^4$, and R$^5$ are, independently, H, hydroxyl, methoxy, or ethoxy, in any combinations thereof; and
wherein
R$^{1\prime}$, R$^{2\prime}$, R$^{3\prime}$, R$^{4\prime}$ and R$^{5\prime}$ are, independently, H, hydroxyl, methoxy, or ethoxy, in any combinations thereof,
or a pharmaceutically acceptable salt thereof,
in an amount effective to suppress angiogenesis in the mammal.

* * * * *